(12) United States Patent
Dickstein et al.

(10) Patent No.: US 11,071,882 B2
(45) Date of Patent: Jul. 27, 2021

(54) BREATHING EQUIPMENT TRAINING

(71) Applicant: Blast Mask, LLC, Dallas, TX (US)

(72) Inventors: Justin Clayton Dickstein, Rockwall, TX (US); Michael R. Moussa, Euless, TX (US); Stephen Hilton Savoie, Everman, TX (US)

(73) Assignee: Blast Mask, LLC, Dallas, TX (US)

( * ) Notice: Subject to any disclaimer, the term of this patent is extended or adjusted under 35 U.S.C. 154(b) by 14 days.

(21) Appl. No.: 16/438,228

(22) Filed: Jun. 11, 2019

(65) Prior Publication Data

US 2019/0290942 A1 Sep. 26, 2019

Related U.S. Application Data

(63) Continuation of application No. 15/676,862, filed on Aug. 14, 2017, now Pat. No. 10,328,293, which is a continuation-in-part of application No. 14/716,709, filed on May 19, 2015, now Pat. No. 9,956,439.

(60) Provisional application No. 62/057,716, filed on Sep. 30, 2014.

(51) Int. Cl.
| | |
|---|---|
| *A62B 18/10* | (2006.01) |
| *A62B 7/00* | (2006.01) |
| *A62B 18/02* | (2006.01) |
| *A63B 23/18* | (2006.01) |
| *A61M 16/20* | (2006.01) |
| *A61M 16/06* | (2006.01) |

(52) U.S. Cl.
CPC ............. *A62B 18/10* (2013.01); *A61M 16/20* (2013.01); *A62B 7/00* (2013.01); *A62B 18/02* (2013.01); *A63B 23/18* (2013.01); *A61M 16/06* (2013.01); *A61M 16/208* (2013.01)

(58) Field of Classification Search
CPC ....... A63B 23/18; A61M 16/06; A61M 16/20; A61M 16/205; A61M 16/206; A61M 16/208; A61M 16/209; A62B 18/00; A62B 18/02; A62B 18/025; A62B 18/04; A62B 18/06; A62B 18/08; A62B 18/10
See application file for complete search history.

(56) References Cited

U.S. PATENT DOCUMENTS

| | | | | |
|---|---|---|---|---|
| 2,642,574 A | * | 6/1953 | Eloranta | A42B 1/046 2/205 |
| 3,871,364 A | * | 3/1975 | Boehringer | A61B 5/0871 600/540 |
| 4,373,520 A | * | 2/1983 | Arbique | A62B 18/08 128/201.19 |
| 4,601,465 A | | 7/1986 | Roy | |

(Continued)

OTHER PUBLICATIONS

Examination Report under Section 18(3) in connection with United Kingdom Application No. GB1706389.2 dated Jan. 6, 2020, 4 pages.

*Primary Examiner* — Joshua Lee

(57) ABSTRACT

A breathing equipment training device and a method for breathing training using a breathing equipment training device. The breathing equipment training device includes a shell and a diaphragm. The shell includes a first opening and a second opening, the first opening configured to be inserted into a breathing opening in a mask to form a connection with the breathing opening of the mask, and the second opening configured to be exposed to ambient air. The diaphragm is positioned in an inner cavity of the shell about the second opening, and configured to impede airflow into the shell through the second opening.

18 Claims, 11 Drawing Sheets

(56) References Cited

U.S. PATENT DOCUMENTS

| | | | | |
|---|---|---|---|---|
| 4,768,520 A * | 9/1988 | Varraux | A61B 5/0871 | 600/538 |
| 4,850,346 A * | 7/1989 | Michel | A62B 18/025 | 128/206.15 |
| 5,579,761 A * | 12/1996 | Yuschak | A62B 23/02 | 128/206.17 |
| 5,627,324 A * | 5/1997 | Shene | A61B 5/0871 | 73/861.53 |
| 5,924,420 A | 7/1999 | Reischel et al. | | |
| 6,450,969 B1 * | 9/2002 | Farr | A61B 5/087 | 600/538 |
| 6,554,746 B1 * | 4/2003 | McConnell | A63B 23/18 | 482/13 |
| 8,342,179 B2 * | 1/2013 | Hacke | A61M 16/1065 | 128/206.15 |
| 8,590,533 B2 * | 11/2013 | Danford | A63B 21/0004 | 128/206.28 |
| 9,067,086 B2 * | 6/2015 | Danford | A63B 21/0085 | |
| 10,086,161 B1 * | 10/2018 | Rashidi | A61M 16/0866 | |
| 2002/0092522 A1 * | 7/2002 | Fabin | A62B 17/04 | 128/201.23 |
| 2003/0041861 A1 * | 3/2003 | Hawkins, Jr. | A62B 7/12 | 128/204.26 |
| 2006/0180153 A1 * | 8/2006 | Schaub | A62B 18/08 | 128/206.16 |
| 2008/0178884 A1 * | 7/2008 | Gerson | A62B 9/02 | 128/206.15 |
| 2008/0257352 A1 * | 10/2008 | Penton | A62B 7/04 | 128/205.24 |
| 2010/0101584 A1 * | 4/2010 | Bledstein | A62B 18/10 | 128/863 |
| 2010/0307506 A1 * | 12/2010 | Kielow | A62B 18/025 | 128/207.12 |
| 2011/0120473 A1 * | 5/2011 | Piper | A61M 16/208 | 128/207.16 |
| 2012/0094806 A1 * | 4/2012 | Danford | A63B 21/0004 | 482/13 |
| 2012/0325205 A1 | 12/2012 | Allum et al. | | |
| 2013/0125896 A1 * | 5/2013 | Dwyer | A62B 23/02 | 128/206.17 |
| 2013/0319420 A1 * | 12/2013 | Danford | A63B 21/0004 | 128/206.21 |
| 2014/0150801 A1 * | 6/2014 | Rusher | A63B 21/0088 | 128/207.16 |
| 2014/0216475 A1 * | 8/2014 | Blomberg | A62B 18/08 | 128/863 |
| 2015/0040907 A1 * | 2/2015 | Hakim | A63B 23/18 | 128/205.24 |
| 2016/0059049 A1 * | 3/2016 | Langford | A62B 18/08 | 128/205.27 |
| 2017/0120084 A1 * | 5/2017 | Tang | A62B 9/04 | |

* cited by examiner

BREATHING EQUIPMENT TRAINING

CROSS-REFERENCE TO RELATED APPLICATIONS

This application is a continuation of U.S. patent application Ser. No. 15/676,862, filed Aug. 14, 2017, which is a continuation in part of U.S. patent application Ser. No. 14/716,709, filed May 19, 2015, now U.S. Pat. No. 9,956,439, which claims priority to U.S. Provisional Patent Application No. 62/057,716 filed on Sep. 30, 2014. The above-identified non-provisional and provisional patent applications are hereby incorporated by reference in their entirety.

TECHNICAL FIELD

The present disclosure relates generally to training equipment. More particularly, the present disclosure relates to training devices and methods for breathing equipment.

BACKGROUND

People working in hostile and potentially hazardous environments, such as, for example, firemen, often use a self-contained breathing apparatus (SCBA) to breathe. For example, oxygen supply may be depleted in the potentially hazardous environment and/or the air in the potentially hazardous environment may not be fit for breathing. Given the risk and potentially hazardous nature, individuals should be properly trained to operate their equipment, such as the SCBA, and have the stamina necessary to perform difficult tasks before being subjected to entering and/or working in such environments. Current solutions fail to provide individuals with the realistic training simulations necessary for the preparation of entering and/or working in such environments.

Accordingly, it would be advantageous to have systems and methods that take into account one or more of the issues discussed above, as well as possibly other issues.

SUMMARY

The different illustrative embodiments of the present disclosure provide an apparatus for a breathing equipment training device and a method for breathing training.

In one embodiment, an apparatus is provided. The apparatus includes a shell and a diaphragm. The shell includes a first opening and a second opening. The first opening is configured to be inserted into a breathing opening in a mask to form a connection with the breathing opening of the mask, and the second opening is configured to be exposed to ambient air. The diaphragm is positioned in an inner cavity of the shell about the second opening. The diaphragm is configured to impede airflow into the shell through the second opening.

In another example embodiment, a method for breathing equipment training is provided. The method comprises attaching, to a mask, a breathing equipment training device that includes a shell and a diaphragm, and breathing through the breathing equipment training device. The shell includes a first opening and a second opening. The first opening is configured to be inserted into a breathing opening in a mask to form a connection with the breathing opening of the mask, and the second opening is configured to be exposed to ambient air. The diaphragm is positioned in an inner cavity of the shell about the second opening. The diaphragm is configured to impede airflow into the shell through the second opening.

In another example embodiment, a breathing equipment training device is provided. The breathing equipment training device includes a shell and a diaphragm. The shell includes a first set of openings, a second set of openings, and a pin. The first set of openings is configured to be inserted into a breathing opening in a mask to form a connection with the breathing opening of the mask. The second set of openings is configured to be exposed to ambient air. The pin is located within the inner cavity of the shell along an axis between the first and second sets of openings and positioned proximate to the second set of openings. The pin is configured to hold the diaphragm in position laterally between the first and second sets of openings. The diaphragm is positioned in an inner cavity of the shell about the second set of openings and is configured to impede airflow into the shell through the second set of openings.

Other technical features may be readily apparent to one skilled in the art from the following figures, descriptions, and claims.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

The various figures and embodiments used to describe the principles of the present disclosure in this patent document are by way of illustration only and should not be construed in any way to limit the scope of the present disclosure. Those skilled in the art will understand that the principles of the present disclosure may be implemented in any type of suitably-arranged device or system.

Various embodiments of the present disclosure recognize and take into account that, for safety reasons, people needing to use breathing equipment, such as, for example, firemen, construction workers, hazardous material response personnel, military personnel, underwater divers, etc., should first train with the equipment. For example, to preserve air supply, an SCBA utilizes on demand breathing. This means that the air flow does not continuously flow into the mask of the wearer of the SCBA. The wearer must manually suck into their mask in order to retrieve air from their air supply. Oftentimes, the amount of force that needs to be used to suck air into the air supply is substantial and/or not common for someone absent specific training.

Various embodiments of the present disclosure further recognize and take into account that use of air or oxygen tanks in the training of personnel to operate breathing equipment is costly. For example, training a person to breathe and suck properly with the breathing equipment can waste air in the tank when the ambient air is perfectly breathable. Accordingly, various embodiments of the present disclosure provide a breathing equipment training device and method that allow people to train to use breathing equipment without needing to have an air tank.

Figure 1:
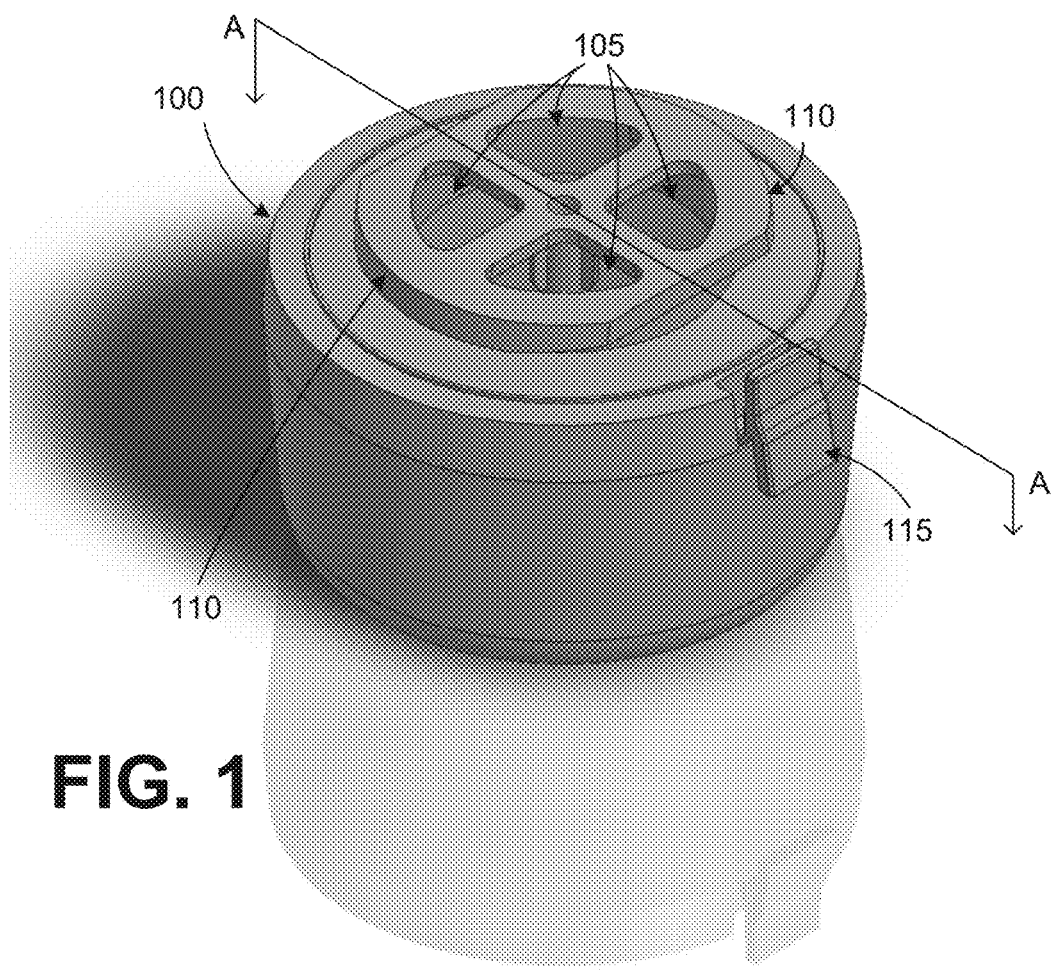
FIG. 1 illustrates a breathing equipment training device in accordance with various embodiments of the present disclosure.

FIG. 1 illustrates a breathing equipment training device 100 in accordance with various embodiments of the present disclosure. In this illustrative embodiment, breathing equipment training device 100 includes a cylindrically-shaped shell with a first set of openings 105 or holes designed to allow air to flow into a mask (e.g., mask 900 in FIG. 9) of an operator of breathing equipment, such as an SCBA. For example, the breathing equipment training device 100 may take the place of a regulator which is attached to the mask to regulate or otherwise control the flow of air into the mask. Breathing equipment training device 100 also includes a raised surface with a pair of flanges 110 that protrude from the breathing equipment training device 100. The flanges 110 are configured to be rotatably inserted into a slot or groove in the opening in the mask to couple or mate the breathing equipment training device 100 to the mask. Breathing equipment training device 100 also includes a latch 115 which locks or fixes the breathing equipment training device 100 to the mask to deter or prevent the breathing equipment training device 100 from rotating inside the opening of the mask and becoming dislodged or disconnected. In this example embodiment, the shell of the breathing equipment training device 100 is a single component, one piece that is not segmentable except through cutting or otherwise destroying the shell. For example, the shell may be a molded plastic or other composite material.

Figure 2:
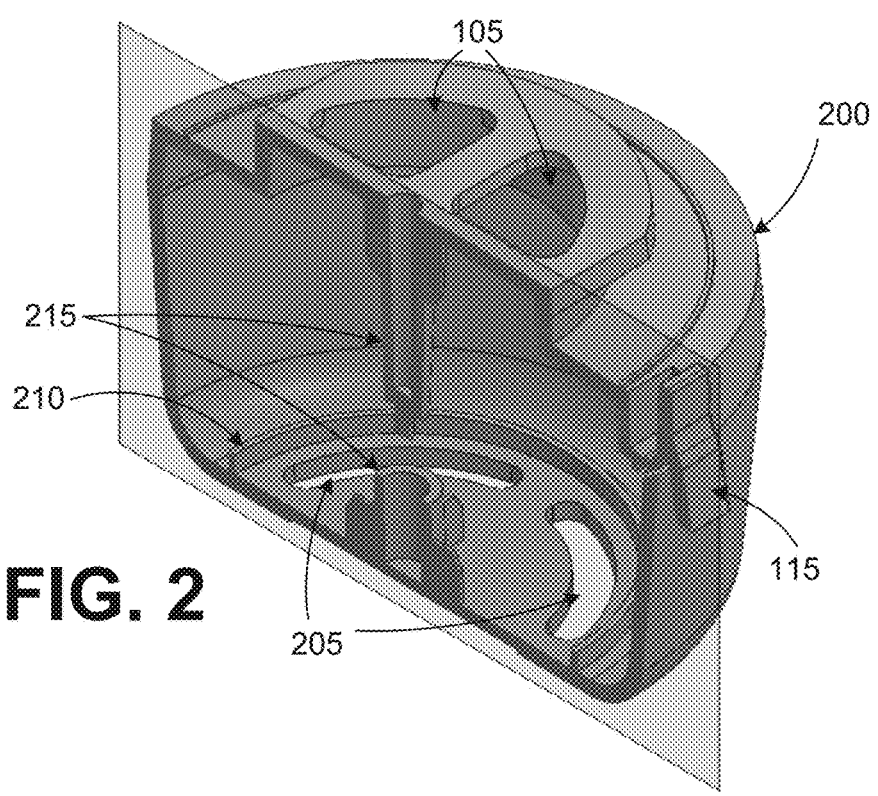
FIG. 2 illustrates a cross-sectional view of a shell for the breathing equipment training device illustrated in FIG. 1.

FIG. 2 illustrates a cross-sectional view of a shell for the breathing equipment training device illustrated in FIG. 1. In this illustrative embodiment, the shell 200 is shown opened along the cross section denoted by line AA in FIG. 1. As illustrated, the shell 200 has a second set of openings 205 or holes seen in the bottom of the shell 200. A raised ring 210 surrounds the second set of openings 205 in the shell 200. Though illustrated with four slot-shaped or circularly-shaped openings or holes, the first and second set of openings 105 and 205 may include any number of different openings or holes of any number of different shapes.

Shell 200 further includes pins 215 which are adapted to receive and hold a diaphragm or valve in place over the second set of openings 205. In this illustrative example, shell 200 does not include a diaphragm or valve as is included in the breathing equipment training device 100. An example diaphragm or valve is depicted in FIG. 8 and illustrated in a bottom portion of the breathing equipment training device 100 in FIG. 7. The diaphragm or valve covers the second set of openings 205 and is made of a flexible material so as to impede or resist (but not completely block) the flow of air and other fluids through the second set of openings 205. For example, the diaphragm or valve may be made from rubber, plastic, polyurethane, a composite material, etc.

In this manner, when attached to a mask, the breathing equipment training device 100 impedes or resists the flow of air into the mask, simulating usage of breathing equipment using on-demand breathing. Different types of diaphragms or valves having different levels of flexibility or resistance to air may be used to simulate, manage, and/or tune different levels of sucking or inhaling that may be required to operate the on-demand breathing equipment. For example, progressively stiffer diaphragms or valves may be inserted into the shell 200 of the breathing equipment training device 100 over time to increase the breathing strength and conditioning of the operator. Additionally, the tightness or snugness with which the diaphragm or valve fits within the shell 200 may be adjusted to simulate, manage, and/or tune different levels of resistance by, for example, increasing or decreasing a width of the diaphragm or valve and/or the shell 200.

Figure 3:
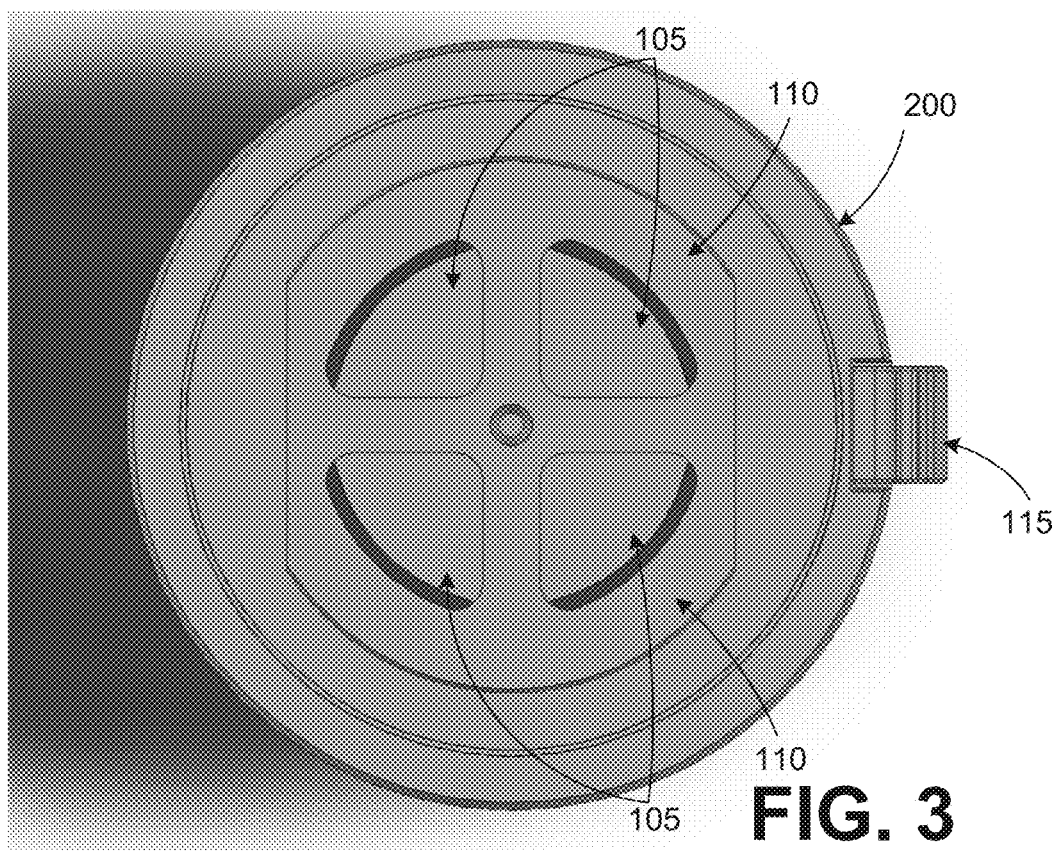
FIG. 3 illustrates a top view of a shell for a breathing equipment training device in accordance with various embodiments of the present disclosure.

FIG. 3 illustrates a top view of shell 200 for breathing equipment training device 100 in accordance with various embodiments of the present disclosure. In this view, the flanges 110, latch 115, and first set of openings 105 are seen.

Figure 4:
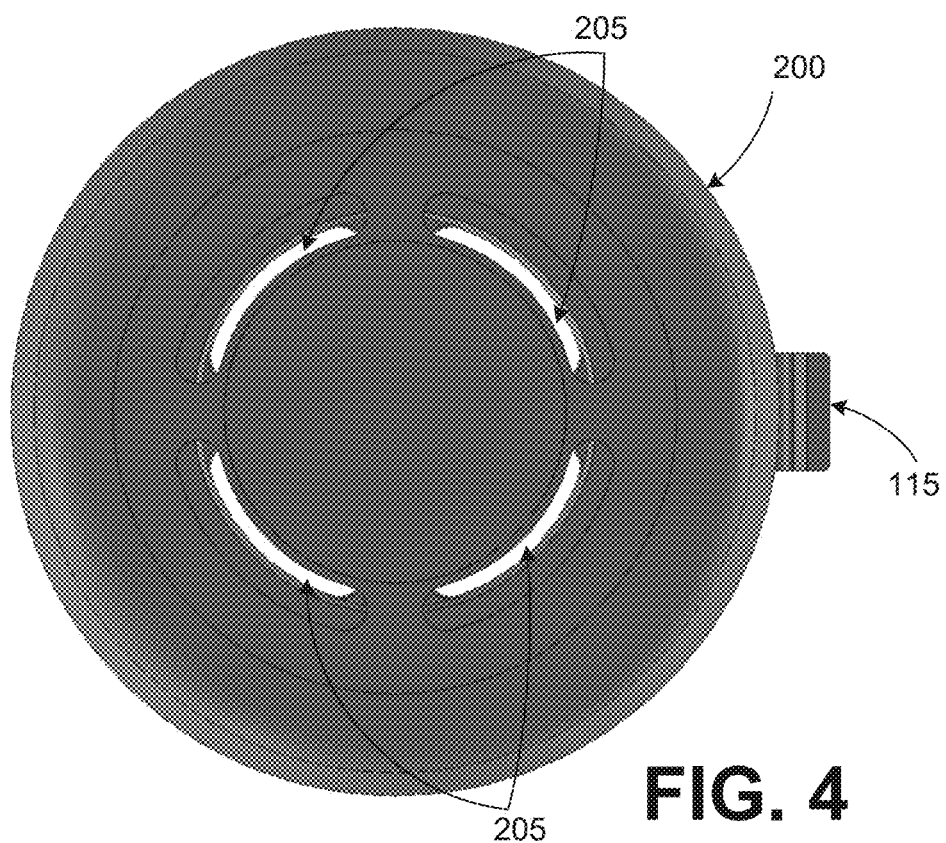
FIG. 4 illustrates a bottom view of a shell for a breathing equipment training device in accordance with various embodiments of the present disclosure.

FIG. 4 illustrates a bottom view of shell 200 for a breathing equipment training device 100 in accordance with various embodiments of the present disclosure. In this view, second set of openings 205 are seen, and through the second set of openings 205, the first set of openings 105 can be seen. In FIGS. 3 and 4, just the shell 200 is present. The diaphragm or valve is not present inside the shell 200. As can be seen, without the diaphragm or valve, air can freely pass through the second set of openings 205 into the shell 200 and out the first set of openings 105. While the terms "top" and "bottom" are used for the convenience of the reader, any side of the breathing equipment training device 100 may be the "top", "bottom", or "side" of the device 100 based on the orientation of the device 100 and the perspective of the viewer.

Figure 5:
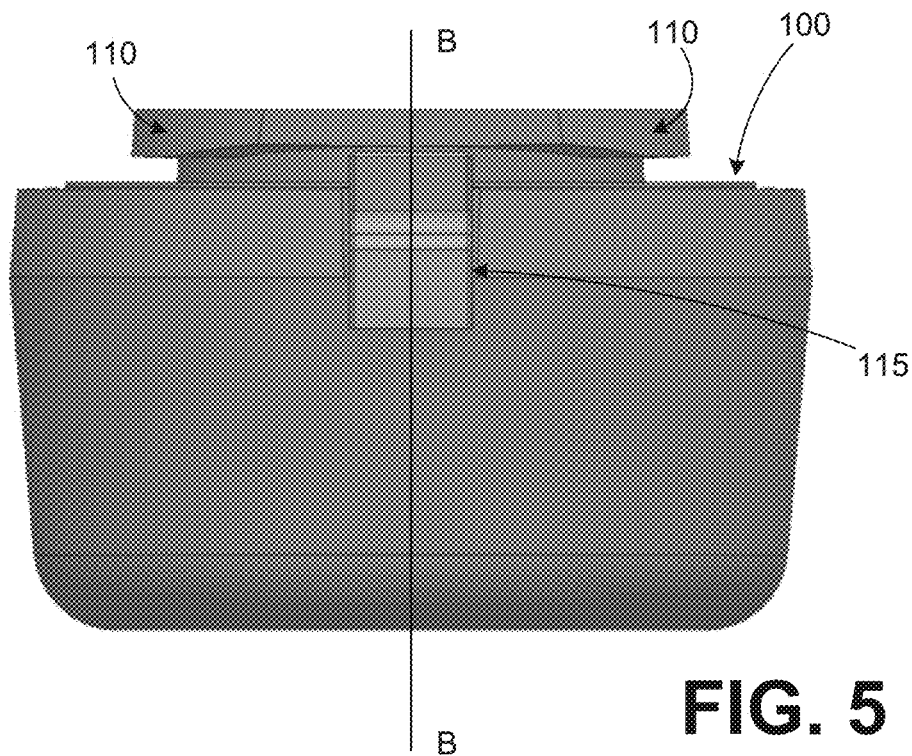
FIG. 5 illustrates a side view of a breathing equipment training device in accordance with various embodiments of the present disclosure.

FIG. 5 illustrates a side view of a breathing equipment training device 100 in accordance with various embodiments of the present disclosure. As illustrated, the flanges 110 protrude out from the raised surface of the breathing equipment training device 100 to connect, seal, or otherwise attach the breathing equipment training device 100 to a mask for breathing equipment.

Figure 6:
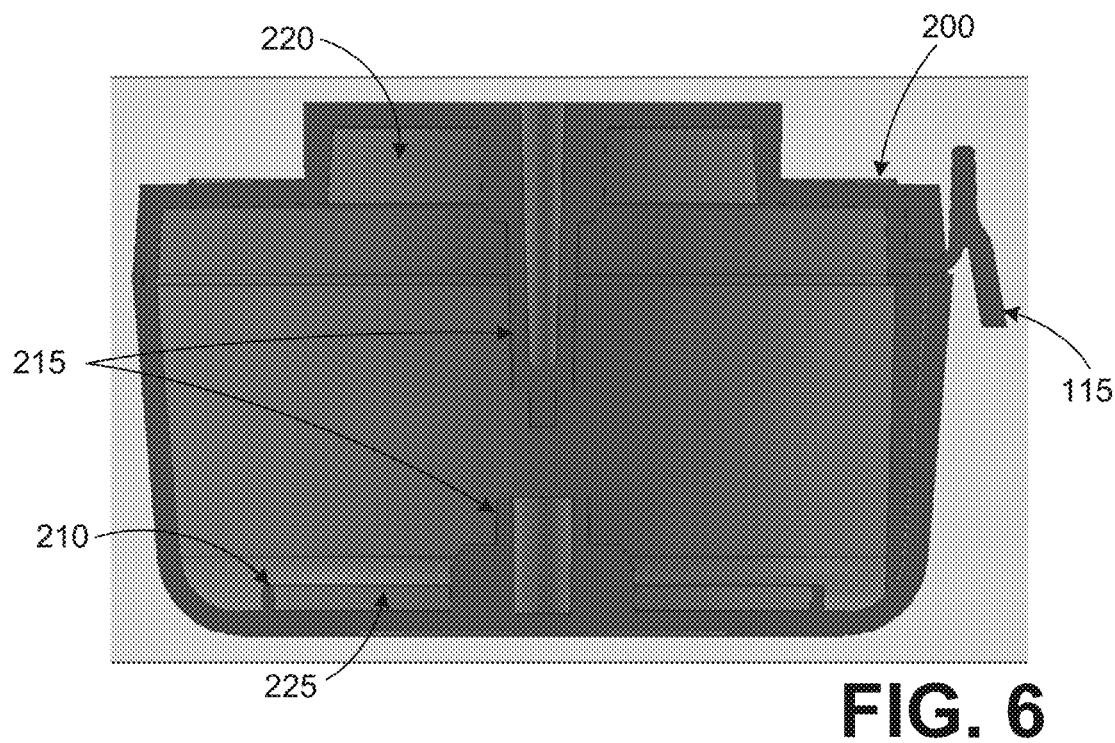
FIG. 6 illustrates a cross-sectional view of a shell for the breathing equipment training device illustrated in FIG. 5.

FIG. 6 illustrates a cross-sectional view of a shell 200 for the breathing equipment training device 100 illustrated in FIG. 5. In this illustrative embodiment, the shell 200 is seen opened along the cross section denoted by line BB in FIG. 5. FIG. 6 also illustrates an important concept of one or more embodiments of the present disclosure that the diameter of the ellipse or circle 220 defining the first set of openings 105 (shown in FIG. 1) is smaller than the ellipse or circle 225 defining the second set of openings 205 (shown in FIG. 2). For example, this configuration simulates a respirator that would be attached to the mask of an SCBA. Additionally, the larger diameter of the second set of openings 205 allows for more surface area for air to enter the mask, which improves the customization of simulating on-demand breathing. For example, the larger surface area of the second set of openings 205 allows for openings in the second set of openings 205 to be larger and allow for more air to enter the shell 200, which allows for the customization of the shell 200 to more closely simulate the on-demand breathing associated with a respirator of an SCBA.

Figure 7:
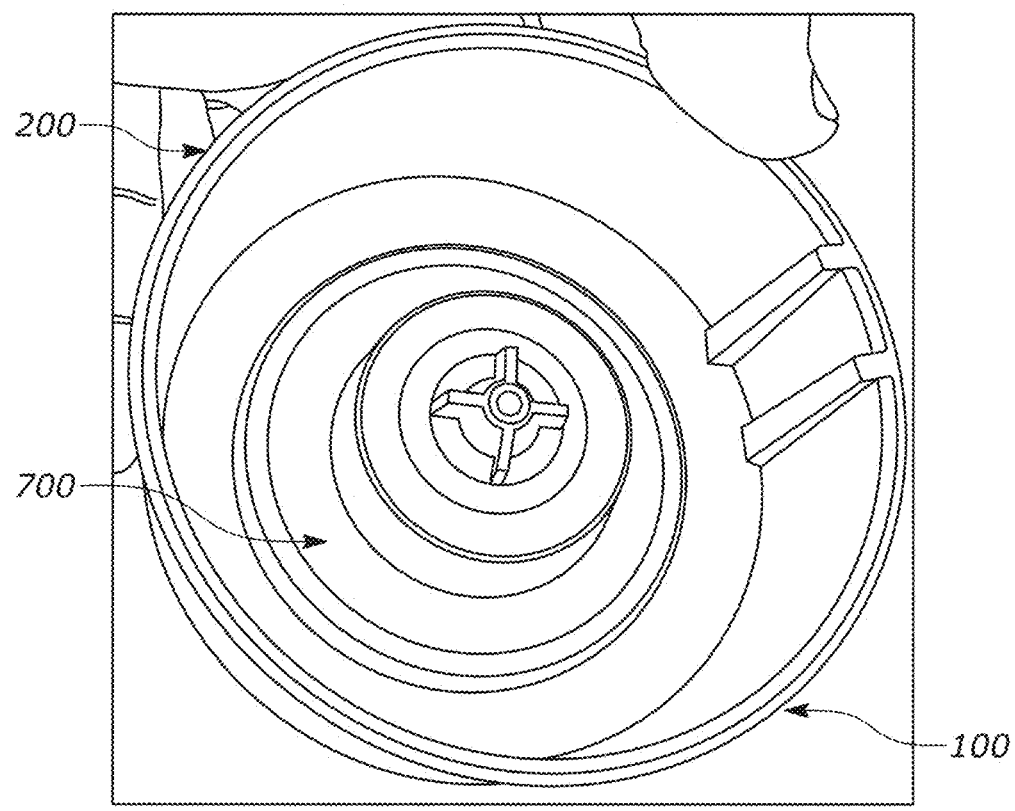
FIG. 7 is an image of the breathing equipment training device with a top portion removed.
Figures 8, 9:
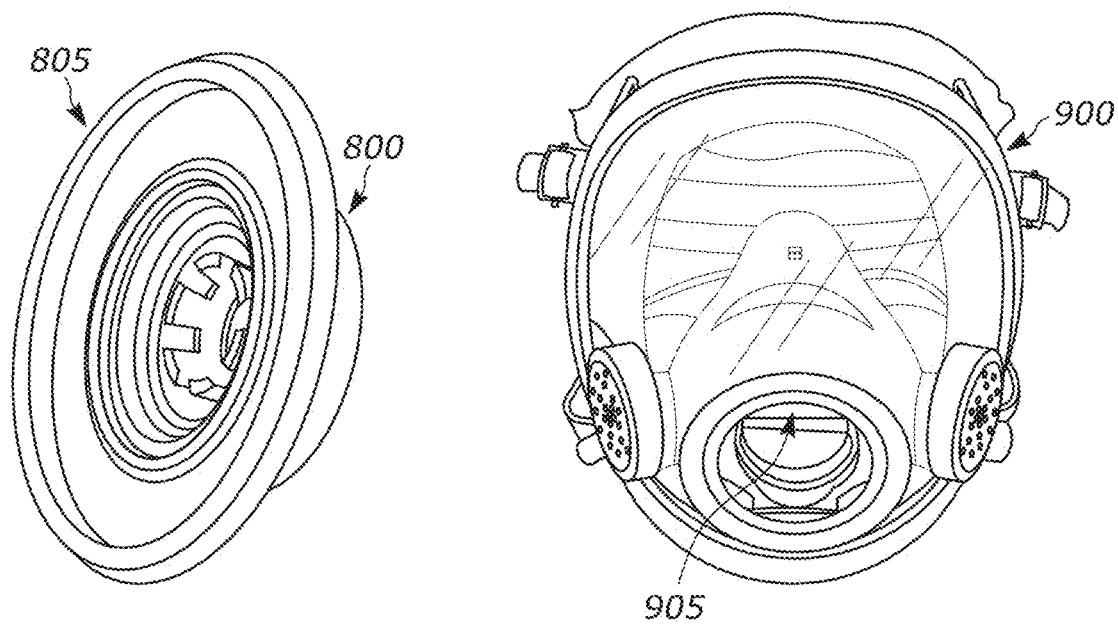
FIG. 8 illustrates a diaphragm insertable in a shell for the breathing equipment training device in accordance with an illustrative embodiment.
FIG. 9 illustrates a mask for an SCBA which may be utilized in implementing various embodiments of the present disclosure.

FIG. 7 is an image of the breathing equipment training device 100 with a top portion removed. In this illustrative embodiment, diaphragm or valve 700 is seen present inside the shell 200 of the device 100, because the top portion of the device 100 has been removed for illustration purposes. Diaphragm or valve 700 covers the second set of openings 205 (not seen in this view) in the bottom of the device 100. As illustrated, the diaphragm or valve 700 tapers outwardly towards the second set of openings 205. In this configuration, a strong sucking or inhaling action away from the second set of openings 205 by the operator of the device 100 can cause the tapered portions of the diaphragm or valve 700 to deform or bend slightly to allow the flow of air into the device 100 around the diaphragm or valve 700. In this illustrative embodiment, blowing or exhaling into the device 100 towards the second set of openings 205 (e.g., exhaling) may be much harder than sucking (e.g., inhaling) given the orientation and tapering of the diaphragm or valve 700 in the shell 200.

FIG. 8 illustrates a diaphragm 800 insertable in the shell 200 for the breathing equipment training device 100 in accordance with an illustrative embodiment. As illustrated, the diaphragm 800 is circularly shaped to cover the second set of openings 205 in the shell (not present in this view). The diaphragm 800 tapers in width from the center to the edges of the diaphragm 800. The diaphragm 800 also includes a ring 805 near and/or along the outer bottom edge of the diaphragm 800. This ring 805 acts as a seal and is matched to seat on or around the ring 210 in the shell 200. In this manner, the ring 805 on the diaphragm 800 and the ring in the shell 200 operate to provide substantially uniform resistance to breathing when operated to consistently and accurately simulate resistance provided by on-demand breathing equipment. While diaphragm 800, ring 805, and ring 210 are depicted as circular, any shape may be used (e.g., ellipse, oval, square, rectangular, etc.).

FIG. 9 illustrates a mask 900 for an SCBA, which may be utilized in implementing various embodiments of the present disclosure. The mask 900 is designed to be worn over the head and face of the operator to protect the eyes, nose, and mouth of the operator in hazardous environments and/or in environments where breathable ambient air is not present. Mask 900 includes a breathing opening 905 matched to be connected to a regulator or the breathing equipment training device 100 of the present disclosure.

Figure 10A:
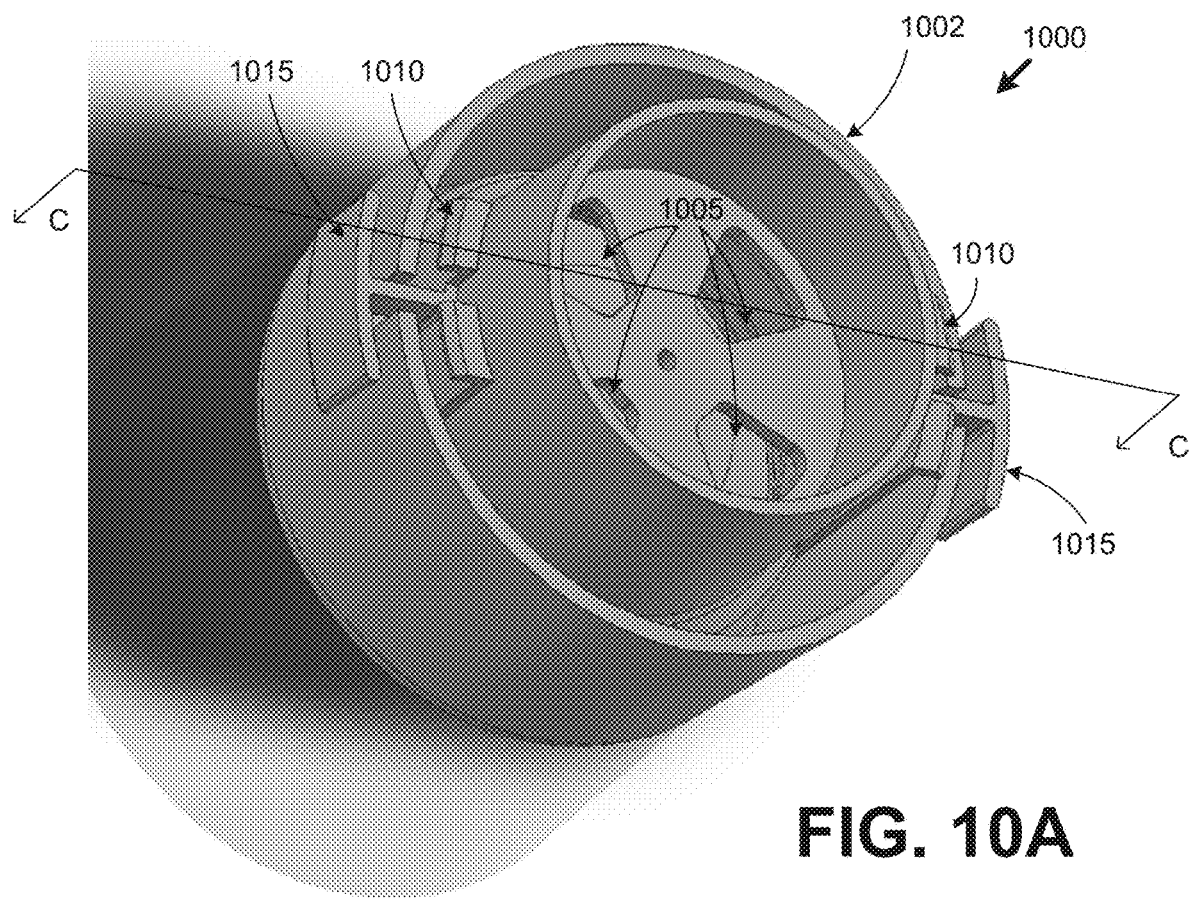
FIG. 10A illustrates another example of a breathing equipment training device in accordance with embodiments of the present disclosure.
Figure 11A:
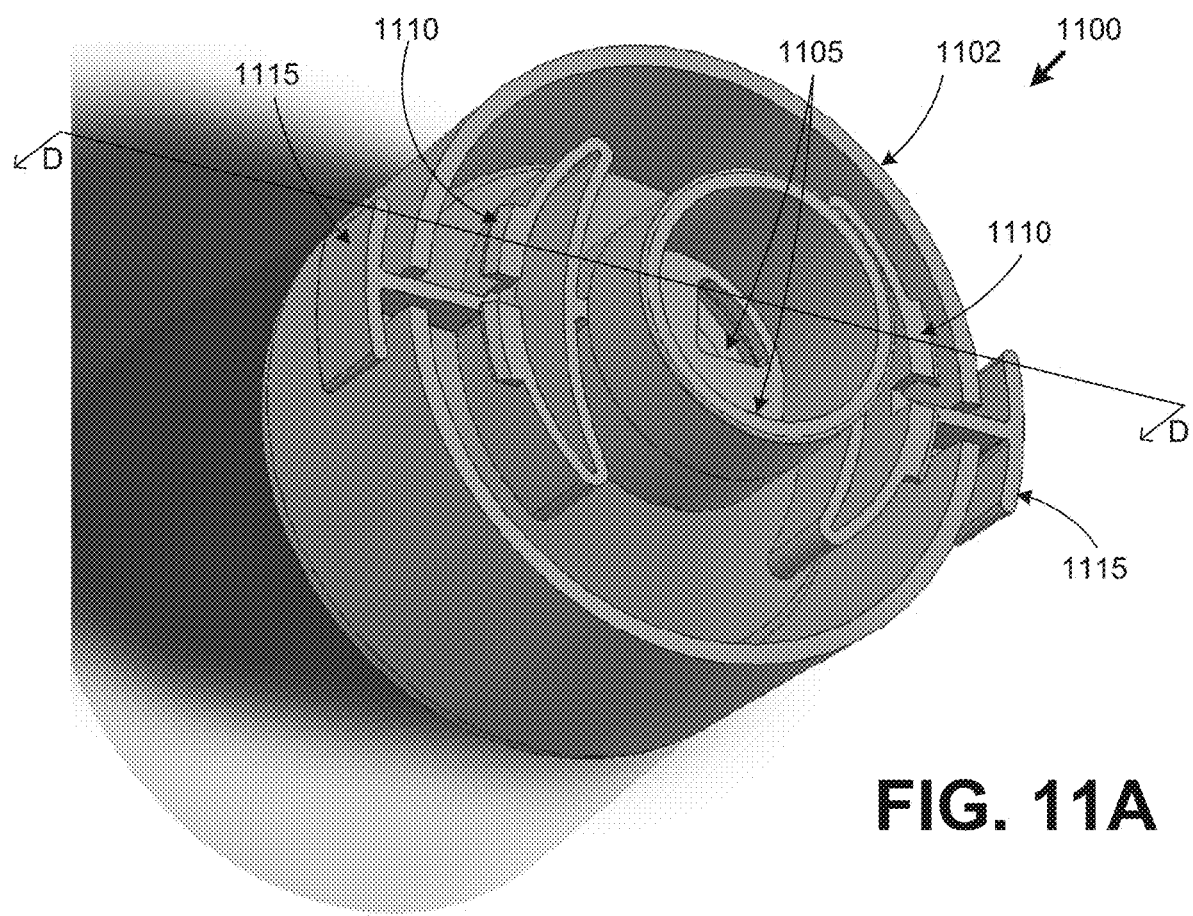
FIG. 11A illustrates another example of a breathing equipment training device in accordance with embodiments of the present disclosure.

FIG. 10A illustrates another example of a breathing equipment training device 1000 in accordance with embodiments of the present disclosure. For example, breathing equipment training device 1000 may be an example implementation of the breathing equipment training device 100 adapted to be inserted into a different type of mask than breathing equipment training device 100. While FIGS. 1, 10A, and 11A illustrate different examples of a breathing equipment training device adapted for use with a particular type of mask, any number of adaptations may be made to the area proximate to the first set of openings 105 to adapt the breathing equipment training device 100 to be inserted into or attached to any number of commercially-available masks.

In this illustrative embodiment, breathing equipment training device 1000 includes a cylindrically-shaped shell 1002 with a first set of openings 1005 or holes in a first opening designed to allow air to flow into a mask (e.g., mask 900 in FIG. 9) of an operator of breathing equipment, such as an SCBA. Breathing equipment training device 1000 also includes flanges 1010 attached to latches 1015, respectively. The flanges 1010 are configured to be inserted into or over slots, grooves, or protrusions, respectively, in the opening in the mask to couple or mate the breathing equipment training device 1000 to the mask. The latches 1015 are depressible to allow the flanges 1010 to be inserted into or removed from the mask for locking or fixing the breathing equipment training device 1000 to the mask. Once attached to the mask, the latches 1015 are also depressible to remove the breathing equipment training device 1000 from the mask.

Figure 10B:
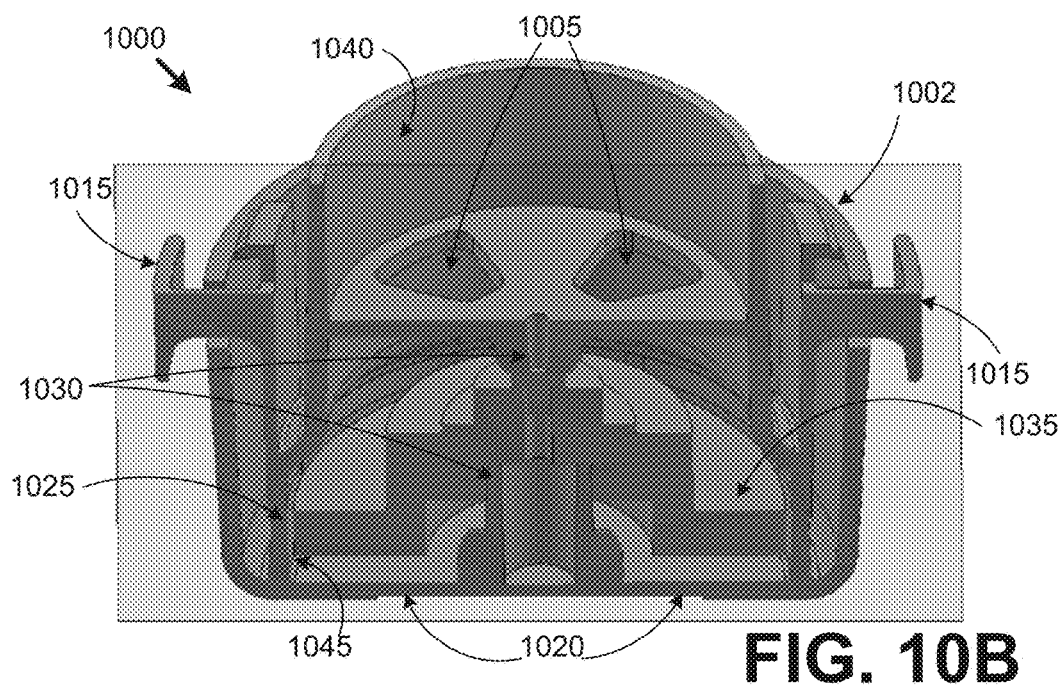
FIG. 10B illustrates a cross-sectional view of the breathing equipment training device illustrated in FIG. 10A.

FIG. 10B illustrates a cross-sectional view of the breathing equipment training device 1000 illustrated in FIG. 10A. In this illustrative embodiment, the breathing equipment training device 1000 is seen opened along the cross section denoted by line CC in FIG. 10A. As illustrated, the shell 1002 has a second set of openings 1020 seen in the bottom of the shell 1002. A ring 1025 surrounds the second set of openings 1020 in the shell 1002 and tapers upwardly toward the first set of openings 1005. Shell 1002 further includes pins 1030, which are adapted to receive and hold the diaphragm or valve 1035 in place over the second set of openings 1020. The diaphragm or valve 1035 may be one example of the diaphragm or valve 700 in FIG. 7.

In this illustrative embodiment, in addition to and/or in lieu of the ways of simulating, managing, and/or tuning different levels of resistance discussed above, different levels of inhalation and/or exhalation resistance may be achieved in breathing equipment training device 1000 by changing the distance between the surface of the shell 1002 proximate the second set of openings 1020 and the diaphragm or valve 1035. For example, the closer the diaphragm or valve 1035 is to the surface of the shell 1002 proximate the second set of openings 1020 the greater the inhalation and/or exhalation resistance becomes. In another example, the ring 1025 may taper inwardly or outwardly as the ring 1025 extends from the surface of the shell 1002 proximate the second set of openings 1020. In this manner, changing the distance between the surface of the shell 1002 proximate the second set of openings 1020 and the diaphragm or valve 1035 allows for adjustment and/or tuning of the tightness or looseness between the ring 1025 and the outer edge of the diaphragm or valve 1035, which also allows for additional or alternative ways of simulating, managing, and/or tuning different levels of inhalation and/or exhalation resistance by the breathing equipment training device 1000. In these examples, the diaphragm or valve 1035 is positioned about the second set of openings 1020, in that the diaphragm or valve 1035 controls, manages, resists, and/or impedes the flow of air into and out of the second set of openings 1020.

FIG. 10B also illustrates that the diameter of the ellipse or circle 1040 defining the first set of openings 1005 is smaller than the ellipse or circle 1045 defining the second set of openings 1020.

FIG. 11A illustrates another example of a breathing equipment training device 1100 in accordance with embodiments of the present disclosure. For example, breathing equipment training device 1100 may be an example implementation of the breathing equipment training device 100 or 1000 adapted to be inserted into a different type of mask than breathing equipment training device 100 or 1000. In this illustrative embodiment, breathing equipment training device 1100 includes a cylindrically-shaped shell 1102 with a first set of openings 1105 in a first opening designed to allow air to flow into a mask (e.g., mask 900 in FIG. 9) of an operator using breathing equipment, such as an SCBA. Breathing equipment training device 1100 also includes flanges 1110 attached to latches 1115, respectively. The flanges 1110 are configured to be inserted into or over slots, grooves, or protrusions, respectively, in the opening in the mask to couple or mate the breathing equipment training device 1100 to the mask. The latches 1115 are depressible to allow the flanges 1110 to be inserted into or removed from the mask for locking or fixing the breathing equipment training device 1100 to the mask. Once attached to the mask, the latches 1115 are also depressible to remove the breathing equipment training device 1100 from the mask.

Figure 11B:
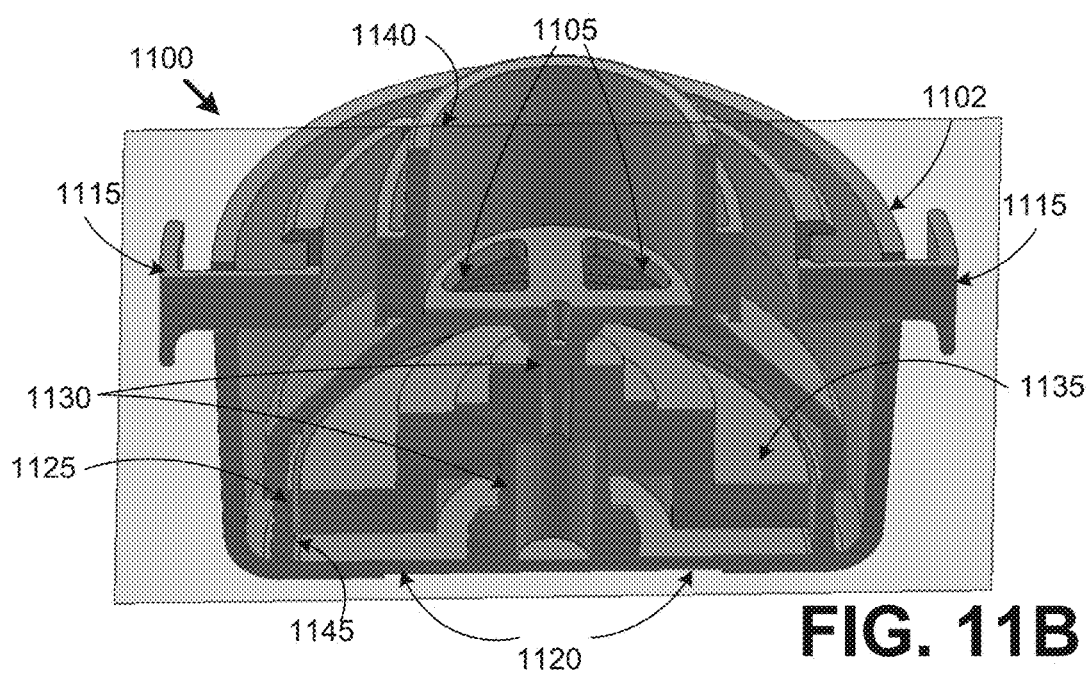
FIG. 11B illustrates a cross-sectional view of the breathing equipment training device illustrated in FIG. 11A.

FIG. 11B illustrates a cross-sectional view of the breathing equipment training device 1100 illustrated in FIG. 11A. In this illustrative embodiment, the breathing equipment training device 1100 is seen opened along the cross section denoted by line DD in FIG. 11A. As illustrated, the shell 1102 has a second set of openings 1120 seen in the bottom of the shell 1102. A ring 1125 surrounds the second set of openings 1120 in the shell 1102 and tapers upwardly toward the first set of openings 1105. Shell 1102 further includes pins 1130, which are adapted to receive and hold the diaphragm or valve 1135 in place over the second set of openings 1120. The diaphragm or valve 1135 may be one example of the diaphragm or valve 700 in FIG. 7.

In this illustrative embodiment, in addition to and/or in lieu of the ways of simulating, managing, and/or tuning different levels of resistance discussed above, different levels of inhalation and/or exhalation resistance may be achieved in breathing equipment training device 1100 by changing the distance between the surface of the shell 1102 proximate the second set of openings 1120 and the diaphragm or valve 1135. For example, the closer the diaphragm or valve 1135 is to the surface of the shell 1102 proximate the second set of openings 1120 the greater the inhalation and/or exhalation resistance becomes. In another example, the ring 1125 may taper inwardly or outwardly as the ring 1125 extends from the surface of the shell 1102 proximate the second set of openings 1120. In this manner, changing the distance between the surface of the shell 1102 proximate the second set of openings 1120 and the diaphragm or valve 1135 allows for adjustment and/or tuning of the tightness or looseness between the ring 1125 and the outer edge of the diaphragm or valve 1135, which also allows for additional or alternative ways of simulating, managing, and/or tuning different levels of inhalation and/or exhalation resistance by the breathing equipment training device 1100. In these examples, the diaphragm or valve 1135 is positioned about the second set of openings 1120, in that the diaphragm or valve 1135 controls, manages, resists, and/or impedes the flow of air into and out of the second set of openings 1120.

FIG. 11B also illustrates that the diameter of the ellipse or circle 1140 defining the first set of openings 1105 is smaller than the ellipse or circle 1145 defining the second set of openings 1120.

Embodiments of the present disclosure also include a method of training to use breathing equipment. In addition to the description above, the method includes attaching the breathing equipment training device 100 to a mask (e.g., mask 900 in FIG. 9) of an operator using breathing equipment, for example, an SCBA. The method further includes breathing through the mask 900 and the breathing equipment training device 100 to train for the on-demand breathing experienced using certain types of breathing equipment. For example, the training may include performing exercises to increase the stamina of the wearer of the breathing equipment training device.

In one or more embodiments, the breathing equipment training device 100 may be a molded plastic device that looks, feels, and weighs about the same as an SCBA regulator. For example, the breathing equipment training device 100 may connect to and secure to the face piece the same as a regulator, and the interior components have a pressure demand—type of inspiration and exhalation valve or components that require the same deliberate breathing efforts as a regular SCBA, without needing to use the air supply of an SCBA.

Most training for use of an SCBA does not require the trainee to need a supply of air, though it is beneficial in realistic training. For example, while wearing an SCBA, a user may need to perform tasks that have a high level of exertion, while the on-demand breathing from the SCBA can make breathing and oxygen supply more difficult than breathing without the SCBA. Embodiments of the present disclosure give the trainee all the physical sensations and demands of being attached to an on-demand air supply without actually using an air supply. This eliminates the need for time consuming, labor-intensive, and costly air refilling support operations, while allowing individuals to be exposed to the demands of SCBA breathing to increase preparedness and stamina.

While various embodiments are described as use of the device 100 in connection with training to use equipment such as an SCBA, in other embodiments, the device 100 may be used in connection with a mask for the purposes of increasing stamina or endurance unrelated to use of equipment such as an SCBA, such as, for example, fitness, cardiovascular, or high-altitude training. In other examples, the device may be used to simulate underwater breathing. For example, the SCBA may be a self-contained underwater breathing apparatus (SCUBA) and the device 100 may be used to simulate and train for on-demand breathing experienced underwater with SCUBA equipment.

Figure 12A:
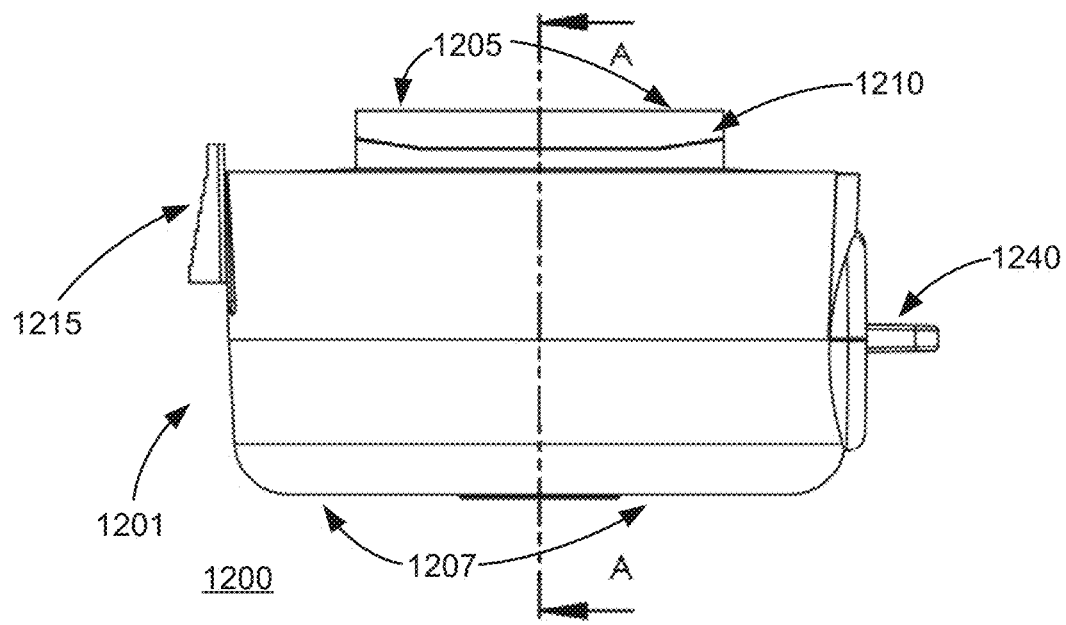
FIG. 12A illustrates a breathing equipment training device in accordance with various embodiments of the present disclosure.
Figure 12B:
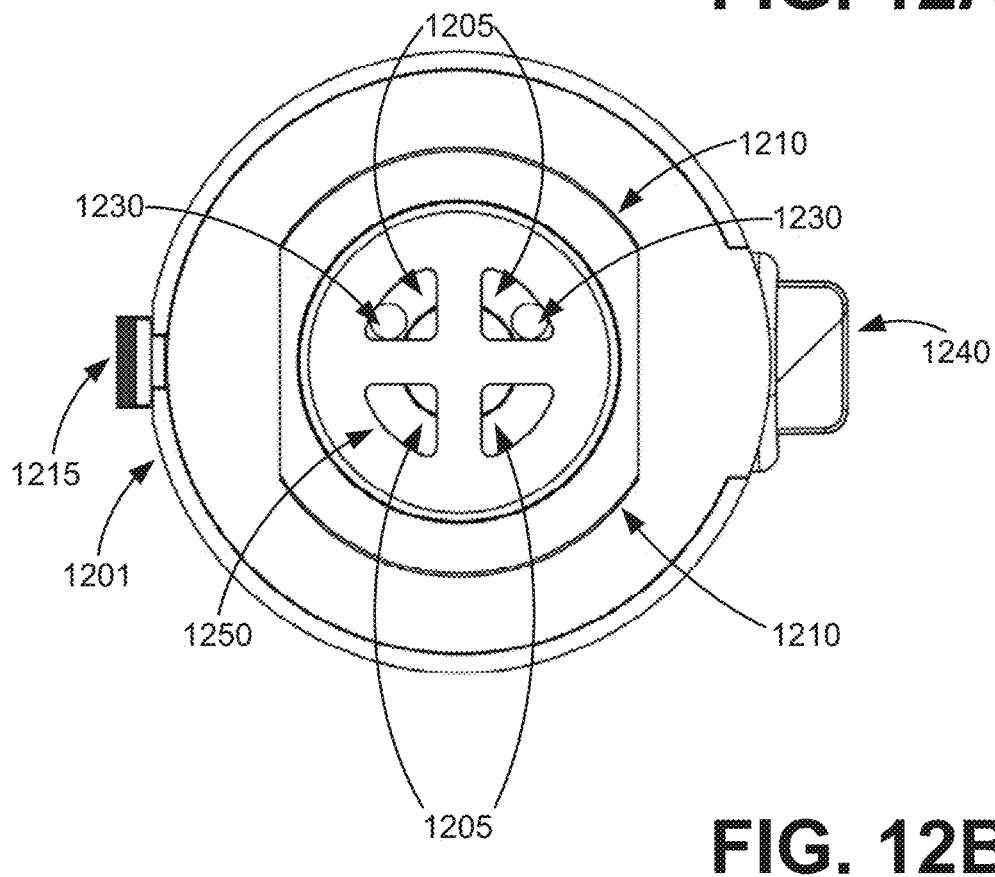
FIG. 12B illustrates a top view of a shell for a breathing equipment training device in accordance with various embodiments of the present disclosure.
Figure 12C:
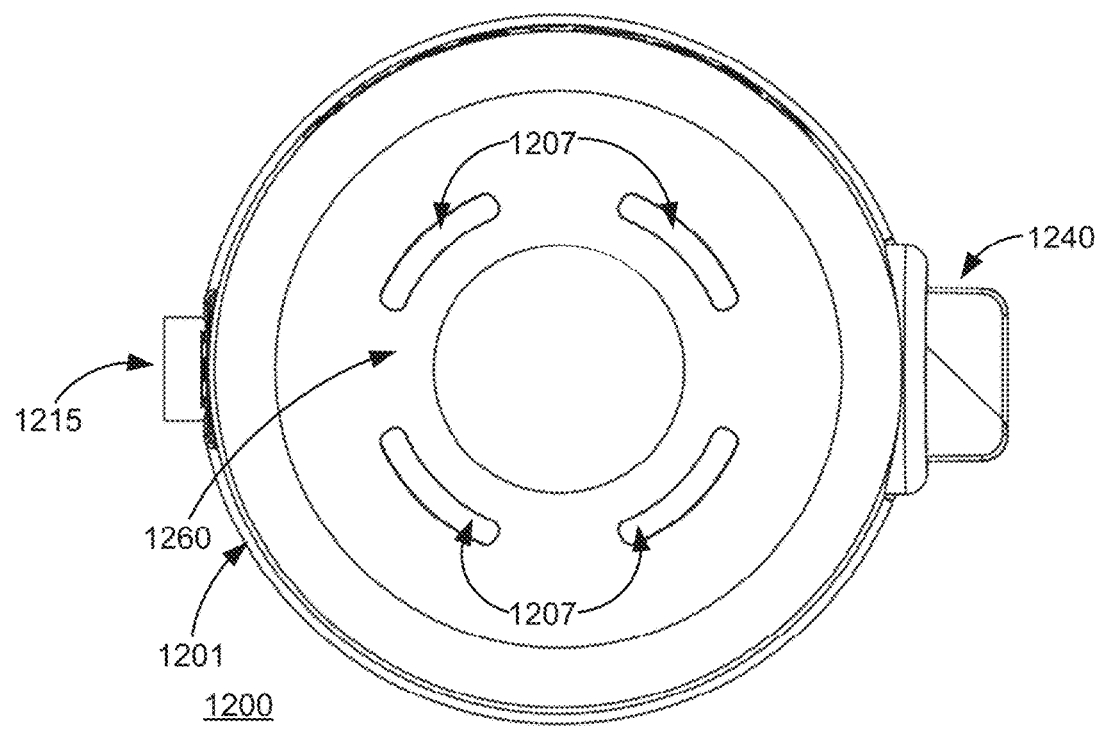
FIG. 12C illustrates a bottom view of a shell for a breathing equipment training device in accordance with various embodiments of the present disclosure.

FIG. 12A illustrates a breathing equipment training device 1200 in accordance with various embodiments of the present disclosure. The device 1200 can be a further embodiment of the device 100. In this illustrative embodiment, breathing equipment training device 1200 includes a cylindrically shaped shell 1201 with a pair of flanges 1210 on either side of the shell 1201, a depressible latch 1215, and a release valve 1240. A first set of openings 1205 and a second set of openings 1207 are not visible in FIG. 12A but are shown in FIGS. 12B and 12C, respectively. The first set of openings 1205 are designed to allow air to flow into a mask (e.g., mask 900 in FIG. 9) of an operator of breathing equipment, such as an SCBA. For example, the breathing equipment training device 1200 may take the place of a regulator which is attached to the mask 900 to regulate or otherwise control the flow of air into the mask 900. The second set of openings 1207 is configured to allow air and/or other fluids to pass into the shell 1201.

The exterior of breathing equipment training device 1200 includes a raised surface with a pair of flanges 1210 that protrude from the breathing equipment training device 1200. The flanges 1210 are configured to be rotatably inserted into a slot or groove in the opening in the mask 900 to couple or mate the breathing equipment training device 1200 to the mask 900. Although shown in this embodiment with a pair of flanges 1210, the raised surface of breathing equipment training device 1200 may include any number of flanges 1210. The exterior of breathing equipment training device 1200 also includes a depressible latch 1215. The depressible latch 1215 is configured to lock or fix the breathing equipment training device 1200 to the mask 900 to prevent the breathing equipment training device 1200 from rotating inside the opening of the mask 900 and becoming dislodged or disconnected. Although shown in this embodiment with one depressible latch 1215, various embodiments may include one or more than one depressible latch 1215. The exterior of breathing equipment training device 1200 also includes a release valve 1240. The release valve 1240 is configured to allow a user to breathe normally after it is rotated about a central axis.

FIG. 12B illustrates a top view of a shell 1201 for a breathing equipment training device in accordance with various embodiments of the present disclosure. In this view, the first set of openings 1205, flanges 1210, the depressible latch 1215, a set of diaphragm holes 1230, the release valve 1240, and a first opening 1250 are seen. The first opening 1250 is a first ellipse or circle configured to be inserted into a breathing opening of a mask, e.g., a mask 900 shown in FIG. 9. The first opening 1250 contains the first set of openings 1205, which is configured to allow air or other fluids to pass through from the shell 1201 to the inside of the mask, e.g., a mask 900 shown in FIG. 9. Though illustrated here with four slot-shaped openings or holes, the first set of openings 1205 may include any number of different openings or holes of any number of different shapes. The set of diaphragm holes 1230 are small holes in a diaphragm 1350. The set of diaphragm holes 1230 and the diaphragm 1350 are discussed in greater detail in the description of FIG. 13A. While the term "top" is used for the convenience of the reader, any side of the breathing equipment training device 1200 may be the "top," "bottom," or "side" of the device 1200 based on the orientation of the device 1200 and the perspective of the viewer.

FIG. 12C illustrates a bottom view of shell 1201 for a breathing equipment training device 1200 in accordance with various embodiments of the present disclosure. In this view, a second set of openings 1207, the depressible latch 1215, the release valve 1240, and a second opening 1260 is seen. The second opening 1260 is a second ellipse or circle configured to allow air and/or other fluids to flow into the shell 1201 through the second set of openings 1207. The second set of openings 1207 is configured to allow air and/or other fluids to freely pass through into the shell 1201. Though illustrated here with four slot-shaped openings or holes, the second set of openings 1207 may include any number of different openings or holes of any number of different shapes. While the term "bottom" is used for the convenience of the reader, any side of the breathing equipment training device 1200 may be the "top", "bottom", or "side" of the device 1200 based on the orientation of the device 1200 and the perspective of the viewer.

Figure 13A:
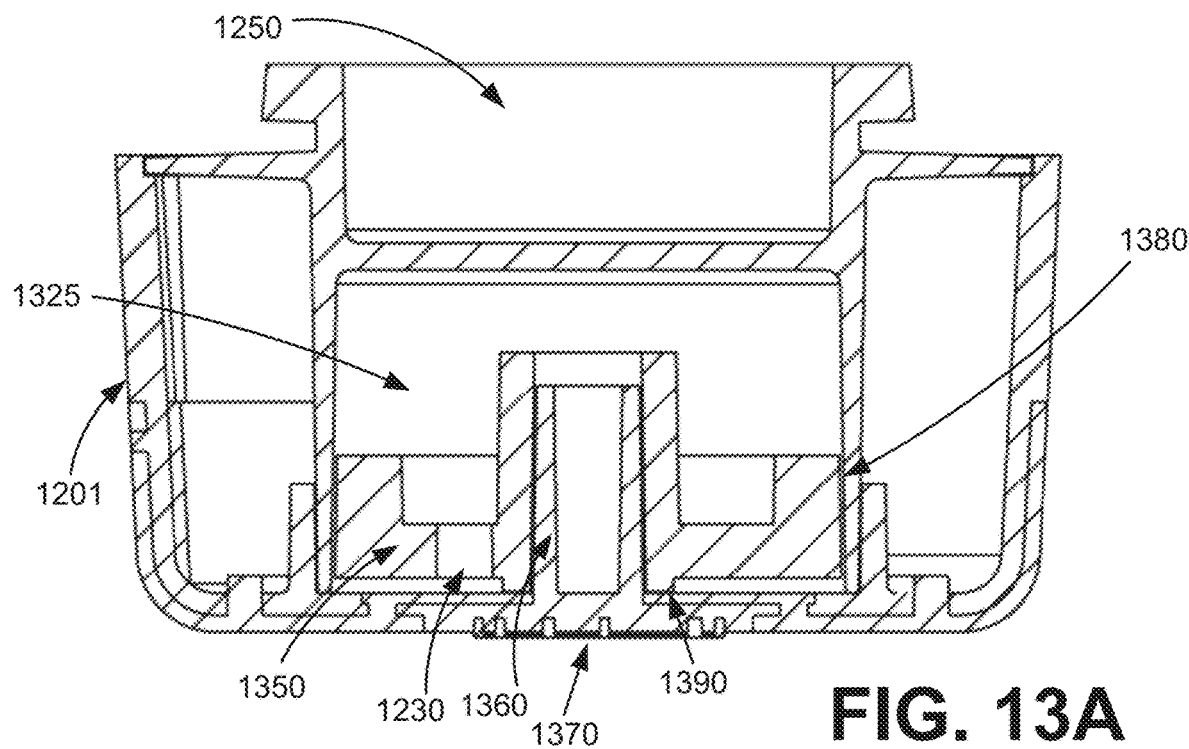
FIG. 13A illustrates a cross-sectional view of a shell for the breathing equipment training device illustrated in FIG. 12A in an exhalation position.

FIG. 13A illustrates a cross-sectional view of a shell for the breathing equipment training device 1200 illustrated in FIG. 12A in the exhalation position. In this illustrative embodiment, the interior of shell 1201 is shown opened along the cross section denoted by line AA in FIG. 12A. In this illustrative embodiment, the device 1200 includes a diaphragm 1350, a pin 1360, a base 1370, and a gap 1380.

Figure 13B:
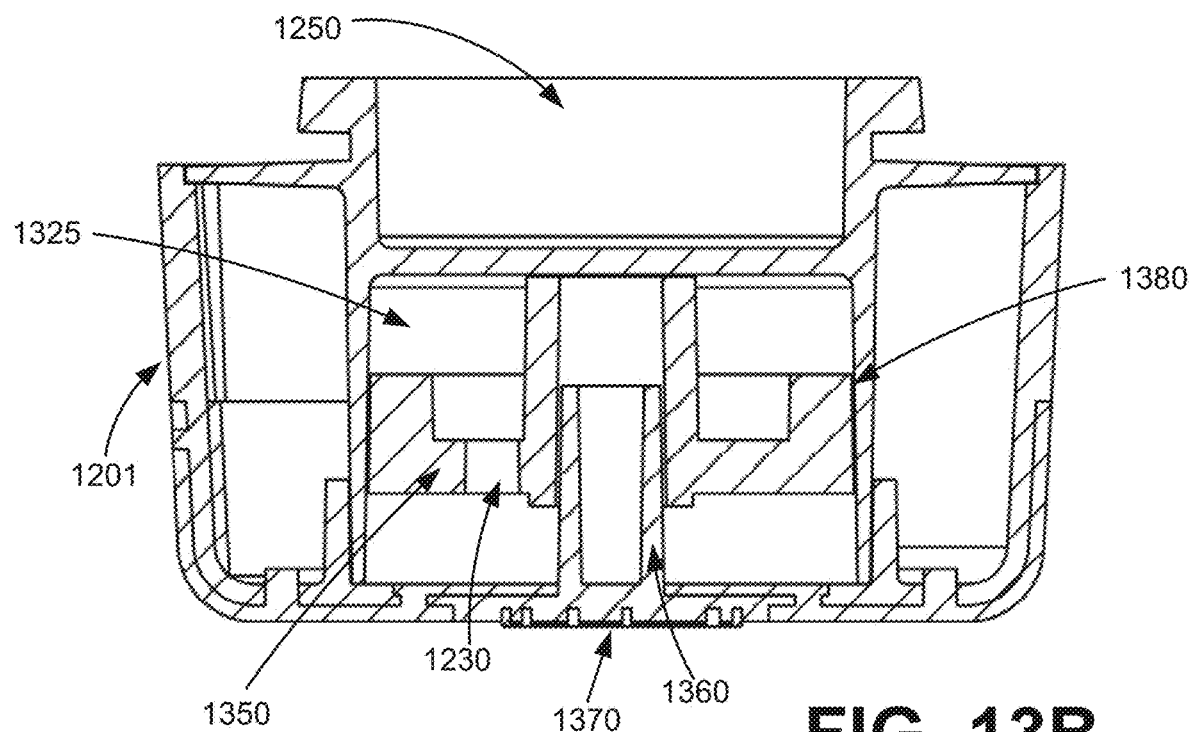
FIG. 13B illustrates a cross-sectional view of a shell for the breathing equipment training device illustrated in FIG. 12A in an inhalation position.

The pin 1360 is configured to guide the diaphragm 1350 between the first set of openings 1205 and the second set of openings 1207 within the shell 1201. In this embodiment, the pin 1360 is cylindrically shaped with a hollow interior to reduce weight. The pin 1360 also narrowly tapers as it extends away from the base 1370 so as to guide the diaphragm 1350 toward the base during exhalation. The diaphragm 1350 is configured to impede or resist (but not completely block) the flow of air and/or other fluids through the second set of openings 1207 and made of a flexible material sufficient to accomplish this function. For example, the diaphragm 1350 may be made from rubber, plastic, polyurethane, a composite material, etc. The diaphragm 1350 is configured to traverse along an axis throughout the shell 1201, guided by the pin 1360. In this embodiment, the pin 1360 does not extend to top of inner cavity 1325 of the shell 1201. The axial length of the pin 1360 serves to prevent or inhibit the diaphragm 1350 from moving laterally within the shell 1201. For example, as shown in FIG. 13B discussed in greater detail below, the pin 1360 guides the diaphragm 1350 along the axis of the pin 1360 with sufficient axil length to maintain the lateral position diaphragm 1350 between the first and second sets of openings 1205 and 1207.

In this embodiment, the diaphragm 1350 is shown in the exhalation position, proximate to the base 1370. When the diaphragm 1350 occupies the exhalation position, as shown here, an inner ring 1390 of the diaphragm 1350 sits flush against the base 1370 about the second opening 1260. Inner ring 1390 serves to raise the majority of the surface of the diaphragm 1350 proximate the base 1370, thereby allowing for additional air to flow through the second set of openings 1207. When the diaphragm 1350 sits flush against the base 1370, the second set of openings 1207 is obscured or partially blocked by the position of the diaphragm 1350. Thereby, the diaphragm 1350 significantly impedes or resists the flow of ambient air or other fluids through the second set of openings 1207.

In this embodiment, when attached to a mask, the breathing equipment training device 1200 impedes or resists flow of air into the mask, simulating usage of breathing equipment using on-demand breathing. Even in this embodiment, the diaphragm 1350 does not completely impede the flow of air into the mask. In one embodiment, throughout the entire circumference of the interior of the shell 1201, a small gap 1380 of between approximately 0.008 in (0.203 mm) and approximately 0.014 in (0.356 mm) is present between the exterior of the diaphragm 1350 and the interior of the shell 1201. In one embodiment, the cumulative area of the gap 1380 between the exterior of the diaphragm 1350 and the interior of the shell 1201 (that is, the area encompassing the entire circumference of the diaphragm 1350) may be between approximately 0.001 in$^2$ (0.645 mm$^2$) and approximately 0.25 in$^2$ (161.29 mm$^2$). In another embodiment, the entire gap 1380 between the exterior of the diaphragm 1350 and the interior of the shell 1201 may be between approximately 0.04 in$^2$ (25.806 mm$^2$) and approximately 0.09 in$^2$ (58.064 mm$^2$). These values can be adjusted to further refine the level of breathing resistance desired for a particular application.

In addition to the gap 1380 between the exterior of the diaphragm 1350 and the shell 1201, the diaphragm 1350 contains small holes 1230 configured to allow air and/or other fluids to pass through the diaphragm 1350. In one illustrative example, the diaphragm 1350 has three holes 1230 evenly spaced 120° apart and equidistant between the interior and exterior edges of the diaphragm. In this embodiment, each hole is approximately 0.20 in (5.08 mm) in diameter. In this embodiment, the diaphragm 1350 contains a total area of approximately 0.094 in$^2$ (60.645 mm$^2$) of space for air or other fluids to pass through. In another embodiment, the diaphragm 1350 contains more than three holes 1230, each comprised of a diameter less than approximately 0.20 in (5.08 mm), which results in a total area of approximately 0.094 in$^2$ (60.645 mm$^2$) of space for air and/or other fluids to pass through. In another embodiment, the diaphragm 1350 contains fewer than three holes 1230, each comprised of a diameter greater than approximately 0.20 in (5.08 mm), which results in a total area of approximately 0.094 in$^2$ (60.645 mm$^2$) of space for air and/or other fluids to pass through. In other embodiments, any number of holes, hole diameter, and total area for passage can be selected to define the amount of breathing resistance desired for a particular application.

FIG. 13B illustrates a cross-sectional view of a shell for the breathing equipment training device 1200 illustrated in FIG. 12A in the inhalation position. In this illustrative embodiment, the shell 1201 is shown opened along the cross section denoted by line AA in FIG. 12A. In this illustrative embodiment, the device 1200 from FIG. 13A is shown with the diaphragm 1350 in a raised position due to inhalation by a user of the device 1200.

For example. when the breathing equipment training device 1200 is connected, or otherwise attached to, a mask (e.g., mask 900 as shown in FIG. 9), a user may breathe through the mask 900 to simulate a scenario in which a mask 900, for example, an SCBA, may need to be worn for protection. In one embodiment, the diaphragm 1350 begins in the exhalation position as shown in FIG. 13A. As a user inhales through the breathing equipment training device 1200, the sucking motion of the user's inhalation causes the diaphragm to traverse along the pin 1360 through the shell 1201 toward the first set of openings 1205. Once the user has finished the inhalation process, he or she will then exhale. The air propelled by the user's exhalation causes the diaphragm 1350 to traverse away from the first set of openings 1205 and along the pin 1360 toward the base 1370 and second set of openings 1207. Once the exhalation process is complete, the diaphragm returns to the exhalation position shown in FIG. 13A. The return of the diaphragm to the exhalation position shown in FIG. 13A concludes one complete breathing cycle by a user.

In various embodiments, as illustrated in FIGS. 13A and 13B, the inner cavity 1325 of the shell 1201 in which the diaphragm 1350 resides tapers from the second set of openings 1207 toward the first opening 1250. Similarly, the outer circumference of the diaphragm 1350 may also taper at a same or different rate. For example, in some embodiments the taper of the inner cavity 1325 of the shell 1201 may be greater than that of the outer circumference of the diaphragm 1350, such that the gap 1380 is reduced (or eliminated) during a breathing cycle (e.g., as illustrated in FIG. 13B). In this manner, greater resistance is provided by the diaphragm 1350 in the inhalation position than in the exhalation position. For example, the increase in breathing resistance during a breathing cycle may force or encourage a user to breathe more slowly or control their breathing despite the resistance so as to obtain more air during a cycle and use fewer breathing cycles.

Other advantages of these embodiments include that the sliding mechanism of the diaphragm 1350 operates to simulate the sound and feel of a traditional breathing equipment device used by, for example, firemen in a potentially hazardous situation. Specifically, one familiar with breathing equipment, e.g., an SCBA, will recognize the clicking sounds produced when the diaphragm 1350 contacts the first set of openings 1205 during the inhalation process and/or contacts the base 1370 at the conclusion of the exhalation process, which is similar to the clicking sound produced by a traditional breathing equipment device that would be used in a potentially hazardous situation.

Another advantage of this embodiment is the simplicity of the design. The design of this embodiment results in a durable product because the diaphragm 1350 is one of only a few moving parts of the breathing equipment training device 1200. Fewer moving parts yields a lesser likelihood of mechanical failures that would result in inoperability of the breathing equipment training device 1200. In addition, the simplicity of this design results in a cost effective manufacturing process. Because the diaphragm 1350 may be made of common industrial products, such as rubber, plastic, polyurethane, a composite material, etc., manufacture of the breathing equipment training device 1200 is not overly burdensome.

Figure 14A:
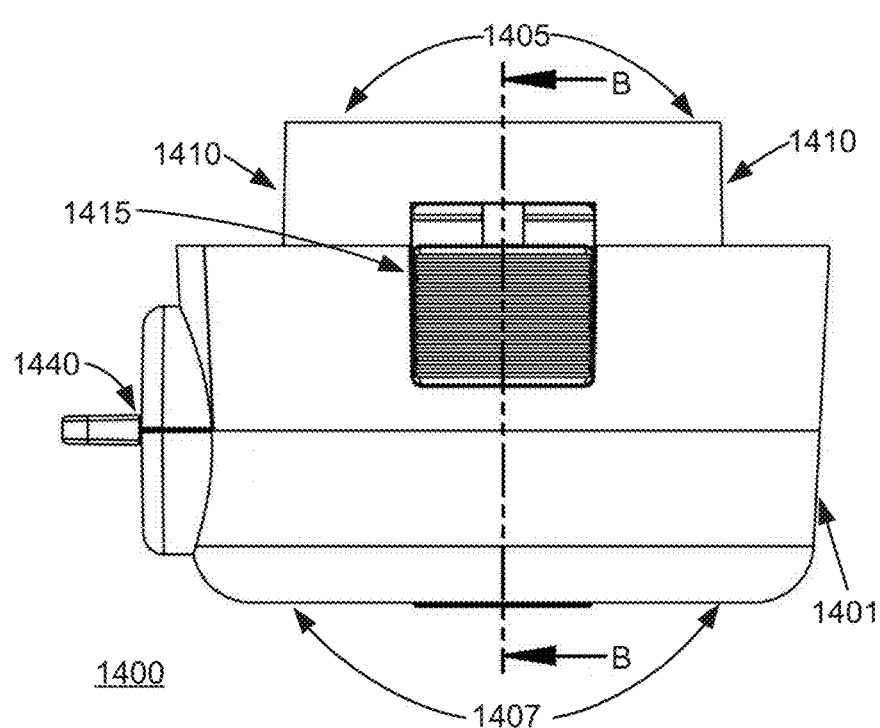
FIG. 14A illustrates a breathing equipment training device in accordance with various embodiments of the present disclosure.

FIG. 14A illustrates a side view of another example of a breathing equipment training device in accordance with various embodiments of the present disclosure. For example, breathing equipment training device 1400 may be an example implementation of the breathing equipment training device 1200 adapted to be inserted into a different type of mask 900 than breathing equipment training device 1200. While FIGS. 14A-15B illustrate examples of a breathing equipment training device adapted for use with a particular type of mask, any number of adaptations may be made to the area proximate to the first set of openings 1405 to adapt the breathing equipment training device 1400 to be inserted into or attached to any number of commercially-available masks.

Figure 14B:
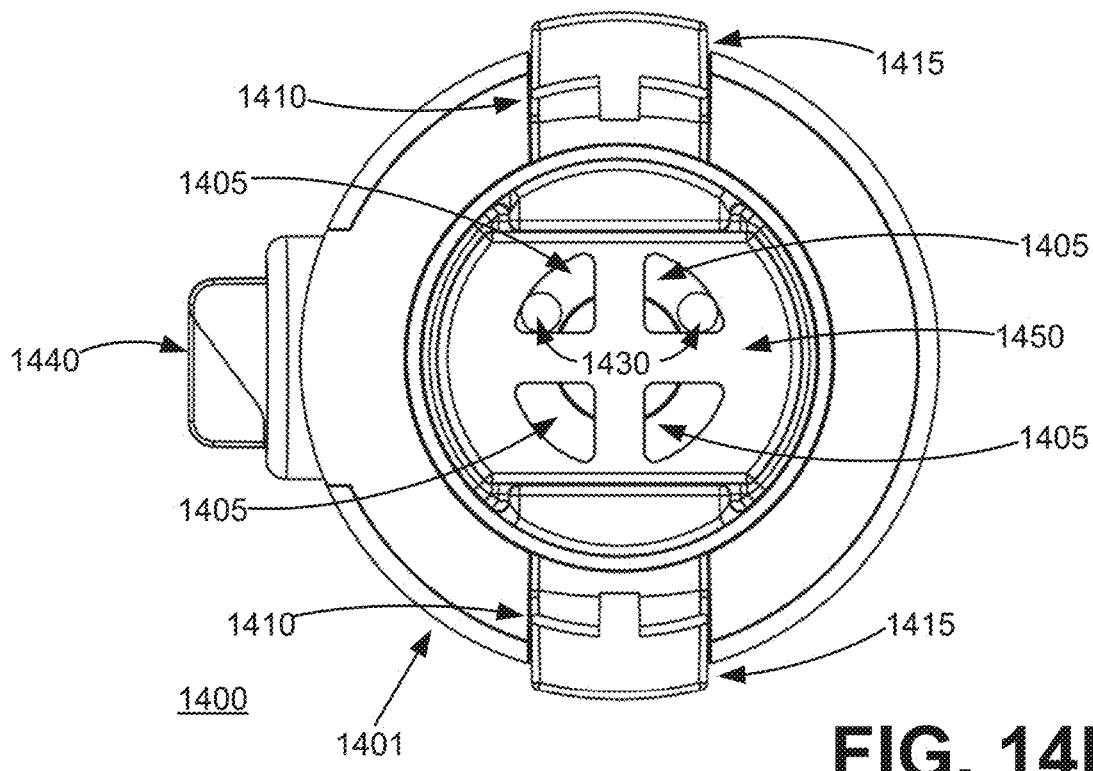
FIG. 14B illustrates a top view of a shell for a breathing equipment training device in accordance with various embodiments of the present disclosure.

In this illustrative embodiment, breathing equipment training device 1400 includes a cylindrically shaped shell 1401 with flanges 1410, depressible latches 1415, and a release valve 1440. A first set of openings 1405 and a second set of openings 1407 are not visible in this illustration. The first set of openings 1405, as seen in FIG. 14B, are designed to allow air to flow into a mask (e.g., mask 900 in FIG. 9) of an operator of breathing equipment, such as an SCBA. For example, the breathing equipment training device 1400 may take the place of a regulator which is attached to the mask to regulate or otherwise control the flow of air into the mask 900. The second set of openings 1407 is configured to allow air or other fluids to pass into the shell 1401.

As illustrated, the flanges 1410 protrude out from the raised surface of the breathing equipment training device 1400 and are configured to connect, seal, or otherwise attach the breathing equipment training device 1400 to a mask for breathing equipment (e.g., mask 900 in FIG. 9). The flanges 1410 are coupled to depressible latches 1415, respectively. The flanges 1410 are configured to be inserted into or over slots, grooves, or protrusions, respectively, in the opening in the mask 900 to couple or mate the breathing equipment training device 1400 to the mask 900. The depressible latches 1415 are depressible to allow the flanges 1410 to be inserted into or removed from the mask 900 for locking or fixing the breathing equipment training device 1400 to the mask 900. Once attached to the mask 900, the depressible latches 1415 are also depressible to remove the breathing equipment training device 1400 from the mask 900.

FIG. 14B illustrates a top view of a shell 1401 for a breathing equipment training device 1400 in accordance with various embodiments of the present disclosure. In this view, a first set of openings 1405, flanges 1410, depressible latches 1415, a set of diaphragm holes 1430, the release valve 1440, and a first opening 1450 are seen. Though illustrated here with four slot-shaped openings or holes, the first set of openings 1405 may include any number of different openings or holes of any number of different shapes. The first opening 1450 is a first circle configured to be inserted into a breathing opening in a mask, e.g., a mask 900 shown in FIG. 9. The set of diaphragm holes 1430 are small holes in a diaphragm 1550. The set of diaphragm holes 1430 and the diaphragm 1550 are discussed in greater detail in the description of FIG. 13A. While the term "top" is used for the convenience of the reader, any side of the breathing equipment training device 1400 may be the "top," "bottom," or "side" of the breathing equipment training device 1400 based on the orientation of the breathing equipment training device 1400 and the perspective of the viewer.

Figure 14C:
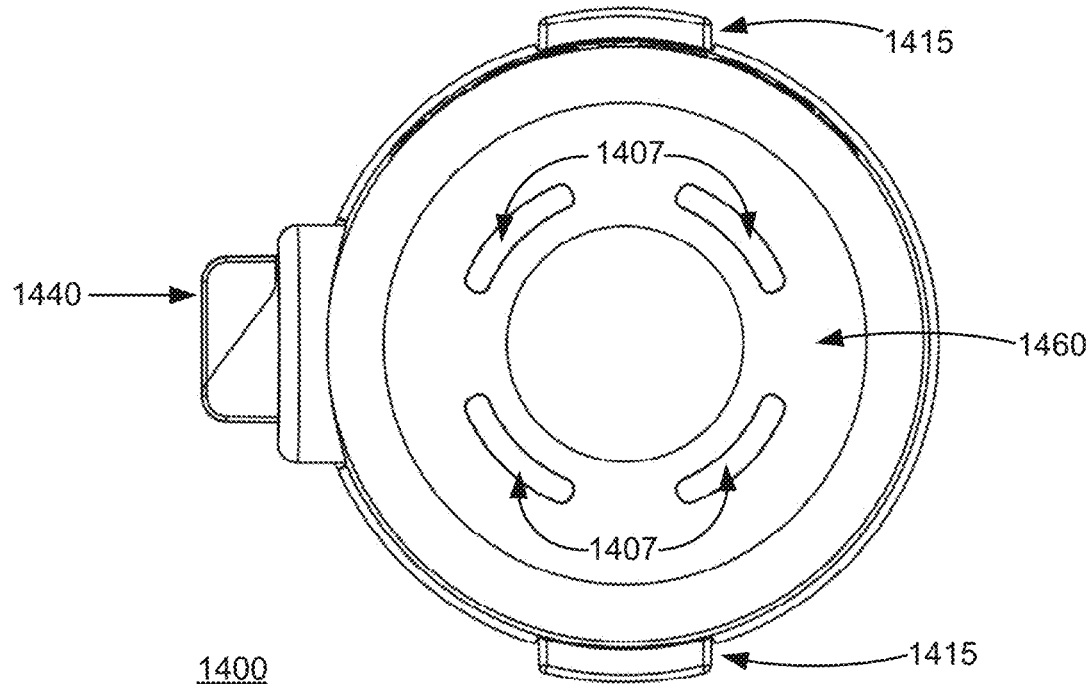
FIG. 14C illustrates a bottom view of a shell for a breathing equipment training device in accordance with various embodiments of the present disclosure.

FIG. 14C illustrates a bottom view of shell 1401 for a breathing equipment training device 1400 in accordance with various embodiments of the present disclosure. In this view, a second set of openings 1407, depressible latches 1415, and the release valve 1440 are shown. The second set of openings 1407 is configured to allow air or other fluids to pass through into the shell 1401. Though illustrated here with four slot-shaped openings or holes, the second set of openings 1407 may include any number of different openings or holes of any number of different shapes. While the term "bottom" is used for the convenience of the reader, any side of the breathing equipment training device 1400 may be the "top", "bottom", or "side" of the breathing equipment training device 1400 based on the orientation of the breathing equipment training device 1400 and the perspective of the viewer.

Figure 15A:
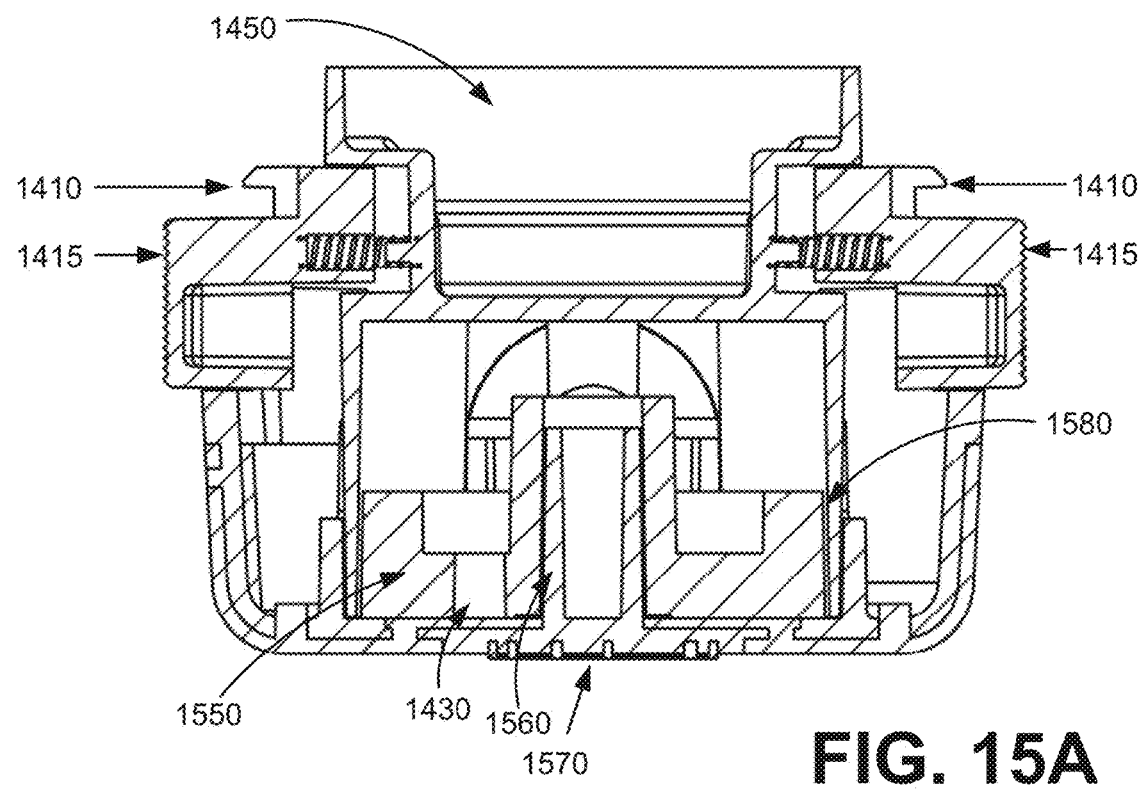
FIG. 15A illustrates a cross-sectional view of a shell for the breathing equipment training device illustrated in FIG. 14A in an exhalation position.

FIG. 15A illustrates a cross-sectional view of a shell for the breathing equipment training device illustrated in FIG. 14A in the exhalation position. In this illustrative embodiment, the interior of shell 1401 is seen opened along the cross section denoted by line BB in FIG. 14A. In this illustrative embodiment, the breathing equipment training device 1400 includes the flanges 1410, the pair of depressible latches 1415, a diaphragm 1550, a pin 1560, a base 1570, and a gap 1580. Hidden from view in this FIG. 15A is the first set of openings 1405 and second set of openings 1407. The diaphragm 1550 and pin 1560 in FIG. 15A operates in the same or similar manner to the diaphragm 1350 in FIG. 13A.

However, in these embodiments, the diaphragm 1550 does not include an inner ring 1390. In this manner, the diaphragm 1550, when in the exhalation position, as illustrated in FIG. 15A, sits flush against the inner surface of the base 1570. Thereby the configuration of the breathing equipment training device 1400 is able to provide greater breathing resistance as desired for a particular application.

Figure 15B:
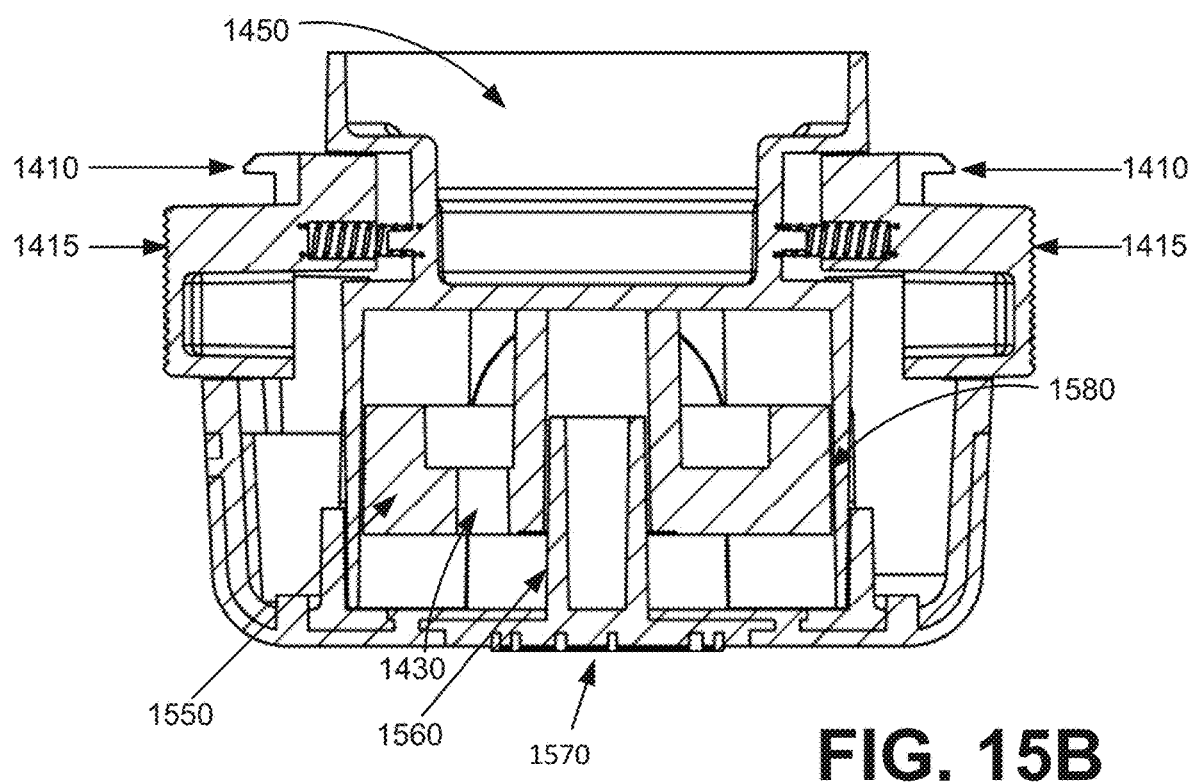
FIG. 15B illustrates a cross-sectional view of a shell for the breathing equipment training device illustrated in FIG. 14A in an inhalation position.

FIG. 15B illustrates a cross sectional view of a shell for the breathing equipment training device illustrated in FIG. 14A in the inhalation position. In this illustrative embodiment, the interior of shell 1401 is seen opened along the cross section denoted by line BB in FIG. 14A. In this illustrative embodiment, the shell 1401 includes the flanges 1410, the depressible latches 1415, the diaphragm 1550, the pin 1560, and the base 1570. Hidden from view in FIG. 15B is the first set of openings 1405 and second set of openings 1407. The diaphragm 1550 in FIG. 15B operates in the same or similar manner to the diaphragm 1350 in FIG. 13B, including the properties of the diaphragm holes 1430 and the gap 1580.

Embodiments of the present disclosure also include a method of training to use breathing equipment. In addition to the description above, the method includes attaching the breathing equipment training device 1200 to a mask, e.g. mask 900 of breathing equipment, for example, an SCBA, via the first opening 1250. The method further includes a user breathing through the mask 900 via the attached breathing equipment training device 1200 to train for the on-demand breathing experienced using certain types of breathing equipment.

Most training for use of an SCBA does not require the trainee to need a supply of air, though it is beneficial in realistic training. For example, while wearing an SCBA, a user may need to perform tasks that have a high level of exertion, while the on-demand breathing from the SCBA can make breathing and oxygen supply more difficult than breathing without the SCBA. Embodiments of the present disclosure give the trainee all the physical sensations and demands of being attached to an on-demand air supply without actually using an air supply. This eliminates the need for time consuming, labor-intensive, and costly air refilling support operations, while allowing individuals to be exposed to the demands of SCBA breathing to increase preparedness and stamina.

While various embodiments are described as use of the device 1200 in connection with training to use equipment such as an SCBA, in other embodiments, the device 1200 may be used in connection with a mask, e.g., mask 900 in FIG. 9, for the purposes of increasing stamina or endurance unrelated to use of equipment such as an SCBA, such as, for example, fitness, cardiovascular, or high-altitude training. In other examples, the device may be used to simulate underwater breathing. For example, the SCBA may be a self-contained underwater breathing apparatus (SCUBA) and the device 1200 may be used to simulate and train for on-demand breathing experienced underwater with SCUBA equipment.

It may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrase "associated with," as well as derivatives thereof, means to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C.

Definitions for other certain words and phrases are provided throughout this patent document. Those of ordinary skill in the art should understand that in many if not most instances, such definitions apply to prior as well as future uses of such defined words and phrases. The descriptions of the various embodiments of the present disclosure have been presented for purposes of illustration but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A breathing equipment training device, the device comprising:
    a shell having first and second openings, a portion of the shell adjacent to the first opening configured to be inserted into a breathing opening in a mask to form a connection with the breathing opening of the mask, the second opening configured to be exposed to ambient air and allow an airflow into the shell; and
    a diaphragm positioned in an inner cavity of the shell about the second opening and configured to impede, but not completely block, the airflow into the shell through the second opening,
    wherein the shell includes a pin located within the inner cavity of the shell and fixed to the shell proximate the second opening, the pin configured to hold the diaphragm in position laterally between the first and second openings, and
    wherein the diaphragm includes one or more holes configured to allow the impeded airflow through the shell.

2. The device of claim 1, wherein:
    the diaphragm is configured to traverse along an outer circumferential surface of the pin along an axis between the first and second openings,
    the pin is further configured to guide the diaphragm along the axis between the first and second openings, and
    the pin is statically fixed to the shell proximate the second opening.

3. The device of claim 2, wherein the inner cavity tapers from the second opening to the first opening such that a gap exists when the diaphragm is in an exhale position proximate to the second opening and the gap is reduced when the diaphragm traverses the axis to an inhale position within the inner cavity.

4. The device of claim 1, wherein an outer circumference of the diaphragm is smaller than an inner circumference of the inner cavity such that a gap is present laterally between the diaphragm and the inner cavity, the gap configured to allow the impeded airflow through the shell.

5. The device of claim 4, wherein the gap has a length between 0.203 mm and 0.356 mm and a surface area of the gap in the cavity is between 0.645 mm$^2$ and 161.29 mm$^2$.

6. The device of claim 1, wherein:
    the first opening includes a first set of openings,
    the second opening includes a second set of openings, and
    the shell is airtight between the first and second sets of openings, with an exception of the first and second sets of openings.

7. The device of claim 1, wherein the shell further includes at least one depressible latch configured to fix the shell to the mask.

8. The device of claim 1, wherein the shell includes a raised surface with a one or more flanges that protrude from the shell, the one or more flanges configured to be inserted into a slot or groove in the opening in the mask to couple the device to the mask.

9. A system comprising the device of claim 1, further comprising the mask configured to cover a mouth and nose of a user, the mask including the breathing opening configured to allow airflow into the mouth of the user.

10. A method for breathing equipment training, the method comprising:
    attaching, to a mask, a breathing equipment training device that includes (i) a shell having first and second openings, a portion of the shell adjacent to the first opening configured to be inserted into a breathing opening in a mask to form a connection with the breathing opening of the mask, the second opening configured to be exposed to ambient air and allow an airflow into the shell and (ii) a diaphragm positioned in an inner cavity of the shell about the second opening and configured to impede, but not completely block, the airflow into the shell through the second opening, wherein the shell includes a pin located within the inner cavity of the shell and fixed to the shell proximate the second opening, the pin configured to hold the diaphragm in position laterally between the first and second openings, and wherein the diaphragm includes one or more holes configured to allow the impeded airflow through the shell; and
    breathing through the breathing equipment training device.

11. The method of claim 10, wherein:
    the diaphragm is configured to traverse along an outer circumferential surface of the pin along an axis between the first and second openings during the breathing,
    the pin is further configured to guide the diaphragm along the axis between the first and second openings, and
    the pin is statically fixed to the shell proximate the second opening.

12. The method of claim 11, wherein the inner cavity tapers from the second opening to the first opening such that a gap exists when the diaphragm is in an exhale position proximate to the second opening and the gap is reduced when the diaphragm traverses the axis to an inhale position within the inner cavity.

13. The method of claim 10, wherein an outer circumference of the diaphragm is smaller than an inner circumference of the inner cavity such that a gap is present laterally between the diaphragm and the inner cavity, the gap configured to allow the impeded airflow through the shell.

14. The method of claim 10, wherein breathing through the breathing equipment training device comprises simulating on-demand breathing associated with a self-contained breathing apparatus.

15. A breathing equipment training device, the device comprising:
- a shell having first and second sets of openings, a portion of the shell adjacent to the first set of openings configured to be inserted into a breathing opening in a mask to form a connection with the breathing opening of the mask, the second set of openings configured to be exposed to ambient air and allow an airflow into the shell; and
- a diaphragm positioned in an inner cavity of the shell about the second set of openings and configured to impede, but not completely block, the airflow into the shell through the second set of openings,
- wherein the shell further includes a pin located within the inner cavity of the shell forming a portion of the shell, the pin extending along an axis between the first and second sets of openings and positioned proximate the second set of openings, the pin configured to hold the diaphragm in position laterally between the first and second sets of openings, and
- wherein the diaphragm includes one or more holes configured to allow the impeded airflow through the shell.

16. The device of claim 15, wherein an outer circumference of the diaphragm is smaller than an inner circumference of the inner cavity such that a gap is present laterally between the diaphragm and the inner cavity, the gap configured to allow the impeded airflow through the shell.

17. The device of claim 16, wherein:
- the diaphragm is configured to traverse along an outer circumferential surface of the pin along the axis between the first and second sets of openings,
- the pin is statically fixed to the shell proximate the second opening,
- the pin configured to guide the diaphragm along the axis between the first and second sets of openings, and
- the inner cavity tapers from the second set of openings to the first set of openings such that the gap exists when the diaphragm is in an exhale position proximate to the second set of openings and the gap is reduced when the diaphragm traverses the axis to an inhale position within the inner cavity.

18. A system comprising the device of claim 15, further comprising the mask configured to cover a mouth and nose of a user, the mask including the breathing opening configured to allow airflow into the mouth of the user.

* * * * *